US010973660B2

(12) United States Patent
Gill et al.

(10) Patent No.: US 10,973,660 B2
(45) Date of Patent: Apr. 13, 2021

(54) POWERED PROSTHETIC THUMB

(71) Applicant: Touch Bionics Limited, Livingston (GB)

(72) Inventors: Hugh Gill, Paisley (GB); Robertus Meijer, Cambridge (GB)

(73) Assignee: Touch Bionics Limited, Livingston (GB)

(*) Notice: Subject to any disclaimer, the term of this patent is extended or adjusted under 35 U.S.C. 154(b) by 81 days.

(21) Appl. No.: 16/219,556

(22) Filed: Dec. 13, 2018

(65) Prior Publication Data
US 2019/0183661 A1 Jun. 20, 2019

Related U.S. Application Data

(60) Provisional application No. 62/599,559, filed on Dec. 15, 2017.

(51) Int. Cl.
A61F 2/58 (2006.01)
A61F 2/70 (2006.01)
(Continued)

(52) U.S. Cl.
CPC ............... A61F 2/586 (2013.01); A61F 2/54 (2013.01); A61F 2/70 (2013.01); A61F 2/76 (2013.01);
(Continued)

(58) Field of Classification Search
CPC .... A61F 2/68; A61F 2/586; A61F 2/70; A61F 2002/587; A61F 2002/6836;
(Continued)

(56) References Cited

U.S. PATENT DOCUMENTS 760,102 A 5/1904 Carnes
1,253,823 A 1/1918 Hobbs
(Continued)

FOREIGN PATENT DOCUMENTS

CN 1803413 7/2006
CN 204274727 4/2015
(Continued)

OTHER PUBLICATIONS

Albu-Schaffer et al., "Soft Robotics", IEEE Robotics & Automation Magazine, Sep. 2008, vol. 15, No. 3, pp. 20-30.
(Continued)

Primary Examiner — Paul B Prebilic
(74) Attorney, Agent, or Firm — Knobbe, Martens, Olson & Bear, LLP

(57) ABSTRACT

Features for a powered prosthetic thumb are described. The thumb provides for rotation of a digit that mimics the natural movement possible with a sound thumb. The thumb may attach to a full or partial prosthetic hand or socket on a residual limb. The thumb may include an upper assembly, including a prosthetic thumb digit, rotatably attached to a mount about a pinch axis and a lateral axis. The digit may rotate about only the pinch axis, only the lateral axis, or both the pinch and lateral axes simultaneously. A first actuator may actuate to cause rotation of the digit about the pinch axis. A second actuator may actuate to cause rotation of the digit about the lateral axis. The first and second actuators may be actuated together at appropriate speeds to cause rotation about both the pinch and lateral axes simultaneously. A swaying chassis may be rotatably connected with the upper assembly and a lower assembly about various offset axes to provide for rotation about the lateral axis.

27 Claims, 22 Drawing Sheets

(51) Int. Cl.
  *A61F 2/76* (2006.01)
  *A61F 2/78* (2006.01)
  *A61F 2/54* (2006.01)
  *A61F 2/68* (2006.01)

(52) U.S. Cl.
  CPC .......... *A61F 2/78* (2013.01); *A61F 2002/587* (2013.01); *A61F 2002/6836* (2013.01); *A61F 2002/6845* (2013.01); *A61F 2002/701* (2013.01); *A61F 2002/707* (2013.01); *A61F 2002/7625* (2013.01); *A61F 2002/7635* (2013.01)

(58) Field of Classification Search
  CPC ........ A61F 2002/6845; A61F 2002/701; A61F 2002/704; A61F 2220/0041; A61F 2220/0058; A61F 2220/0091; A61F 2250/0006; A61F 2250/0096; A61F 2/76; A61F 2/78; A61F 2002/7635
  See application file for complete search history.

(56) References Cited

U.S. PATENT DOCUMENTS

| | | |
|---|---|---|
| 1,507,682 A | 9/1924 | Pecorella et al. |
| 1,507,683 A | 9/1924 | Pecorella et al. |
| 2,445,711 A | 7/1948 | Fitch |
| 2,477,463 A | 7/1949 | Otterman |
| 2,482,555 A | 9/1949 | Otterman |
| 2,508,156 A | 5/1950 | Gillman |
| 2,516,791 A | 7/1950 | Motis et al. |
| 2,549,716 A | 4/1951 | Simpson |
| 2,586,293 A | 2/1952 | Birkigt |
| 2,592,842 A | 4/1952 | Alderson |
| 2,669,727 A | 2/1954 | Opuszenski |
| 2,983,162 A | 5/1961 | Musser |
| 3,406,584 A | 10/1968 | Roantree |
| 3,509,583 A | 5/1970 | Fraioli |
| 3,582,857 A | 6/1971 | Kishel |
| 3,641,832 A | 2/1972 | Shigeta et al. |
| 3,683,423 A | 8/1972 | Crapanzano |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 4,030,141 A | 6/1977 | Graupe |
| 4,044,274 A | 8/1977 | Ohm |
| 4,084,267 A | 4/1978 | Zadina |
| 4,094,016 A | 6/1978 | Eroyan |
| 4,114,464 A | 9/1978 | Schubert et al. |
| 4,197,592 A | 4/1980 | Klein |
| 4,398,110 A | 8/1983 | Flinchbaugh et al. |
| 4,558,704 A | 12/1985 | Petrofsky |
| 4,577,127 A | 3/1986 | Ferree et al. |
| 4,623,354 A | 11/1986 | Childress et al. |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,955,918 A | 9/1990 | Lee |
| 4,960,425 A | 10/1990 | Yan et al. |
| 4,990,162 A | 2/1991 | LeBlanc et al. |
| 5,020,162 A | 6/1991 | Kersten et al. |
| 5,062,673 A | 11/1991 | Mimura |
| 5,088,125 A | 2/1992 | Ansell et al. |
| 5,133,775 A | 7/1992 | Chen |
| 5,246,463 A | 9/1993 | Giampapa |
| 5,252,102 A | 10/1993 | Singer et al. |
| 5,387,245 A | 2/1995 | Fay et al. |
| 5,413,611 A | 5/1995 | Haslam, II et al. |
| 5,498,472 A | 3/1996 | Gold |
| 5,501,498 A | 3/1996 | Ulrich |
| 5,581,166 A | 12/1996 | Eismann et al. |
| 5,605,071 A | 2/1997 | Buchanan, Jr. |
| 5,785,960 A | 7/1998 | Rigg et al. |
| 5,851,194 A | 12/1998 | Fratrick |
| 5,852,675 A | 12/1998 | Matsuo et al. |
| 5,888,213 A | 3/1999 | Sears et al. |
| 5,888,246 A | 3/1999 | Gow |
| 6,111,973 A | 8/2000 | Holt et al. |
| 6,175,962 B1 | 1/2001 | Michelson |
| 6,223,615 B1 | 5/2001 | Huck |
| 6,244,873 B1 | 6/2001 | Hill et al. |
| 6,344,062 B1 | 2/2002 | Abboudi et al. |
| 6,361,570 B1 | 3/2002 | Gow |
| 6,517,132 B2 | 2/2003 | Matsuda et al. |
| 6,591,707 B2 | 7/2003 | Torii et al. |
| 6,660,043 B2 | 12/2003 | Kajitani et al. |
| 6,786,112 B2 | 9/2004 | Ruttor |
| 6,896,704 B1 | 5/2005 | Higuchi et al. |
| 6,908,489 B2 | 6/2005 | Didrick |
| 6,918,622 B2 | 7/2005 | Kim et al. |
| 7,144,430 B2 | 12/2006 | Archer et al. |
| 7,243,569 B2 | 7/2007 | Takahashi et al. |
| 7,316,304 B2 | 1/2008 | Heravi et al. |
| 7,316,795 B1 | 1/2008 | Knauss |
| 7,370,896 B2 | 5/2008 | Anderson et al. |
| 7,481,782 B2 | 1/2009 | Scott et al. |
| 7,640,680 B1 | 1/2010 | Castro |
| 7,655,051 B2 | 2/2010 | Stark |
| 7,823,475 B2 | 11/2010 | Hirabayashi et al. |
| 7,867,287 B2 | 1/2011 | Puchhammer |
| 7,922,773 B1 | 4/2011 | Kuiken |
| 8,016,893 B2 | 9/2011 | Weinberg et al. |
| 8,052,185 B2 | 11/2011 | Madhani |
| 8,100,986 B2 | 1/2012 | Puchhammer et al. |
| 8,197,554 B2 | 6/2012 | Whiteley et al. |
| 8,257,446 B2 | 9/2012 | Puchhammer |
| 8,337,568 B2 | 12/2012 | Macduff |
| 8,343,234 B2 | 1/2013 | Puchhammer |
| 8,491,666 B2 | 7/2013 | Schulz |
| 8,579,991 B2 | 11/2013 | Puchhammer |
| 8,593,255 B2 | 11/2013 | Pang et al. |
| 8,657,887 B2 | 2/2014 | Gill |
| 8,662,552 B2 | 3/2014 | Torres-Jara |
| 8,663,339 B2 | 3/2014 | Inschlag et al. |
| 8,690,963 B2 | 4/2014 | Puchhammer |
| 8,696,763 B2 | 4/2014 | Gill |
| 8,739,315 B2 | 6/2014 | Baacke |
| 8,747,486 B2 | 6/2014 | Kawasaki et al. |
| 8,795,387 B1 | 8/2014 | Razink |
| 8,803,844 B1 | 8/2014 | Green et al. |
| 8,808,397 B2 | 8/2014 | Gow |
| 8,828,096 B2 | 9/2014 | Gill |
| 8,900,327 B2 | 12/2014 | Bertels et al. |
| 8,915,528 B2 | 12/2014 | Haslinger |
| 8,951,303 B2 | 2/2015 | Dehoff et al. |
| 8,979,943 B2 | 3/2015 | Evans et al. |
| 8,984,736 B2 | 3/2015 | Radocy |
| 8,986,395 B2 | 3/2015 | McLeary |
| 8,995,760 B2 | 3/2015 | Gill |
| 8,999,003 B2 | 4/2015 | Wenstrand et al. |
| 9,016,744 B2 | 4/2015 | Starkey |
| 9,017,422 B2 | 4/2015 | Locker |
| 9,039,057 B2 | 5/2015 | Schvalb et al. |
| 9,071,170 B2 | 6/2015 | Baba et al. |
| 9,072,614 B2 | 7/2015 | Starkey et al. |
| 9,072,616 B2 | 7/2015 | Schulz |
| 9,114,028 B2 | 8/2015 | Langenfeld et al. |
| 9,278,012 B2 | 3/2016 | Gill |
| 9,320,621 B2 | 4/2016 | Iversen et al. |
| 9,333,096 B2 | 5/2016 | Perez de Alderete et al. |
| 9,364,364 B2 | 6/2016 | Williams |
| 9,370,430 B2 | 6/2016 | Macduff |
| 9,375,319 B2 | 6/2016 | Macduff |
| 9,375,325 B2 | 6/2016 | Garrec et al. |
| 9,381,099 B2 | 7/2016 | Perry et al. |
| 9,387,095 B2 | 7/2016 | McLeary et al. |
| 9,402,749 B2 | 8/2016 | Gill et al. |
| 9,435,400 B2 | 9/2016 | Cheung et al. |
| 9,456,909 B2 | 10/2016 | Johnson et al. |
| 9,463,085 B1 | 10/2016 | Theobald |
| 9,463,100 B2 | 10/2016 | Gill |

(56) References Cited

U.S. PATENT DOCUMENTS

| | | |
|---|---|---|
| 9,468,540 B2 | 10/2016 | Nagatsuka et al. |
| 9,474,630 B2 | 10/2016 | Veatch |
| 9,474,631 B2 | 10/2016 | Veatch |
| 9,510,958 B2 | 12/2016 | Mori |
| 9,579,218 B2 | 2/2017 | Lipsey et al. |
| 9,579,219 B2 | 2/2017 | Amend, Jr. et al. |
| 9,585,771 B2 | 3/2017 | Baba et al. |
| 9,592,134 B2 | 3/2017 | Varley |
| 9,629,731 B2 | 4/2017 | Thompson, Jr. et al. |
| 9,636,270 B2 | 5/2017 | Miyazawa |
| 9,707,103 B2 | 7/2017 | Thompson, Jr. et al. |
| 9,720,515 B2 | 8/2017 | Wagner et al. |
| 9,730,813 B2 | 8/2017 | Evans et al. |
| 9,737,418 B2 | 8/2017 | Veatch |
| 9,744,055 B2 | 8/2017 | Engeberg et al. |
| 9,814,604 B2 | 11/2017 | Jury |
| 9,839,534 B2 | 12/2017 | Lipsey et al. |
| 9,861,499 B2 | 1/2018 | Sensinger |
| 9,877,848 B2 | 1/2018 | Ikebe |
| 9,889,059 B2 | 2/2018 | Arakawa |
| 9,913,737 B2 | 3/2018 | Hunter |
| 9,931,229 B2 | 4/2018 | Veatch |
| 9,974,667 B1 | 5/2018 | Cazenave |
| 9,999,522 B2 | 6/2018 | Gill |
| 10,004,611 B2 | 6/2018 | Iversen et al. |
| 10,004,612 B2 | 6/2018 | Iversen et al. |
| 10,022,248 B2 | 7/2018 | Thompson, Jr. et al. |
| 10,028,880 B2 | 7/2018 | Arata et al. |
| 10,034,780 B2 | 7/2018 | Lipsey et al. |
| 10,045,865 B2 | 8/2018 | Veatch |
| 10,045,866 B2 | 8/2018 | Armbruster |
| 10,052,216 B2 | 8/2018 | Moyer et al. |
| 10,076,425 B2 | 9/2018 | Farina et al. |
| 10,092,423 B2 | 10/2018 | Goldfarb et al. |
| 10,265,197 B2 | 4/2019 | Gill et al. |
| 10,318,863 B2 | 6/2019 | Lock et al. |
| 10,369,016 B2 | 8/2019 | Lipsey et al. |
| 10,369,024 B2 | 8/2019 | Gill |
| 10,398,576 B2 | 9/2019 | Gill et al. |
| 10,449,063 B2 | 10/2019 | Gill |
| 10,610,385 B2 | 4/2020 | Meijer et al. |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2003/0090115 A1 | 5/2003 | Kim et al. |
| 2004/0002672 A1 | 1/2004 | Carlson |
| 2004/0054423 A1 | 3/2004 | Martin |
| 2004/0078299 A1 | 4/2004 | Down-Logan et al. |
| 2004/0103740 A1 | 6/2004 | Townsend et al. |
| 2004/0181289 A1 | 9/2004 | Bedard et al. |
| 2004/0182125 A1 | 9/2004 | McLean |
| 2005/0021154 A1 | 1/2005 | Brimalm |
| 2005/0021155 A1 | 1/2005 | Brimalm |
| 2005/0093997 A1 | 5/2005 | Dalton et al. |
| 2005/0101693 A1 | 5/2005 | Arbogast et al. |
| 2005/0102037 A1 | 5/2005 | Matsuda |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0032884 A1 | 2/2007 | Veatch |
| 2007/0058860 A1 | 3/2007 | Harville et al. |
| 2007/0061111 A1 | 3/2007 | Jung et al. |
| 2007/0071314 A1 | 3/2007 | Bhatti et al. |
| 2007/0102228 A1 | 5/2007 | Shiina et al. |
| 2007/0137351 A1 | 6/2007 | Schwendemann |
| 2007/0230832 A1 | 10/2007 | Usui et al. |
| 2007/0260328 A1 | 11/2007 | Bertels et al. |
| 2007/0276303 A1 | 11/2007 | Jenner, Jr. |
| 2008/0058668 A1 | 3/2008 | Seyed Momen et al. |
| 2008/0097269 A1 | 4/2008 | Weinberg et al. |
| 2008/0146981 A1 | 6/2008 | Greenwald et al. |
| 2008/0215162 A1 | 9/2008 | Farnsworth et al. |
| 2008/0260218 A1 | 10/2008 | Smith et al. |
| 2008/0262634 A1 | 10/2008 | Puchhammer |
| 2009/0145254 A1 | 6/2009 | Hirabayashi et al. |
| 2009/0213379 A1 | 8/2009 | Carroll et al. |
| 2010/0016990 A1 | 1/2010 | Kurtz |
| 2010/0116078 A1 | 5/2010 | Kim |
| 2010/0274365 A1 | 10/2010 | Evans et al. |
| 2011/0048098 A1 | 3/2011 | Rollins et al. |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |
| 2012/0004884 A1 | 1/2012 | Fillol et al. |
| 2012/0014571 A1 | 1/2012 | Wong et al. |
| 2012/0061155 A1 | 3/2012 | Berger et al. |
| 2012/0099788 A1 | 4/2012 | Bhatti et al. |
| 2012/0109337 A1 | 5/2012 | Schulz |
| 2012/0204665 A1 | 8/2012 | Baudasse |
| 2012/0280812 A1 | 11/2012 | Sheikman et al. |
| 2012/0286629 A1 | 11/2012 | Johnson et al. |
| 2012/0303136 A1 | 11/2012 | Macduff |
| 2012/0330439 A1 | 12/2012 | Goldfarb et al. |
| 2013/0041476 A1 | 2/2013 | Schulz |
| 2013/0053984 A1 | 2/2013 | Hunter et al. |
| 2013/0076699 A1 | 3/2013 | Spencer |
| 2013/0144197 A1 | 6/2013 | Ingimundarson et al. |
| 2013/0175816 A1 | 7/2013 | Kawasaki et al. |
| 2013/0226315 A1 | 8/2013 | Varley |
| 2013/0253705 A1 | 9/2013 | Goldfarb et al. |
| 2013/0268090 A1 | 10/2013 | Goldfarb et al. |
| 2013/0268094 A1 | 10/2013 | Van Wiemeersch |
| 2013/0310949 A1 | 11/2013 | Goldfarb et al. |
| 2014/0060236 A1 | 3/2014 | Watanabe |
| 2014/0148918 A1 | 5/2014 | Pedersen et al. |
| 2014/0148919 A1 | 5/2014 | Pedersen et al. |
| 2014/0236314 A1 | 8/2014 | Van Wiemeersch |
| 2014/0251056 A1 | 9/2014 | Preuss |
| 2014/0277588 A1 | 9/2014 | Patt et al. |
| 2014/0324189 A1 | 10/2014 | Gill et al. |
| 2014/0371871 A1 | 12/2014 | Farina et al. |
| 2015/0112448 A1 | 4/2015 | Scott et al. |
| 2015/0142082 A1 | 5/2015 | Simon et al. |
| 2015/0183069 A1 | 7/2015 | Lee |
| 2015/0190245 A1 | 7/2015 | McLeary et al. |
| 2015/0216679 A1* | 8/2015 | Lipsey ............... A61F 2/583 623/24 |
| 2015/0216681 A1 | 8/2015 | Lipsey et al. |
| 2015/0230941 A1 | 8/2015 | Jury |
| 2015/0351935 A1 | 12/2015 | Donati et al. |
| 2015/0360369 A1 | 12/2015 | Ishikawa et al. |
| 2015/0374515 A1* | 12/2015 | Meijer ............... A61F 2/72 623/25 |
| 2016/0089251 A1 | 3/2016 | Mandl et al. |
| 2016/0166409 A1 | 6/2016 | Goldfarb et al. |
| 2016/0250044 A1 | 9/2016 | Iversen et al. |
| 2016/0287422 A1 | 10/2016 | Kelly et al. |
| 2016/0296345 A1 | 10/2016 | Deshpande et al. |
| 2016/0367383 A1 | 12/2016 | Sensinger et al. |
| 2017/0007424 A1 | 1/2017 | Gill |
| 2017/0049586 A1 | 2/2017 | Gill et al. |
| 2017/0168565 A1 | 6/2017 | Cohen et al. |
| 2017/0281368 A1 | 10/2017 | Gill |
| 2017/0340459 A1 | 11/2017 | Mandelbaum |
| 2018/0036145 A1* | 2/2018 | Jury ............... A61L 27/56 |
| 2018/0064563 A1 | 3/2018 | Gill |
| 2018/0071115 A1 | 3/2018 | Lipsey et al. |
| 2018/0098862 A1 | 4/2018 | Kuiken et al. |
| 2018/0116829 A1 | 5/2018 | Gaston et al. |
| 2018/0133032 A1 | 5/2018 | Poirters |
| 2018/0140441 A1 | 5/2018 | Poirters |
| 2018/0168830 A1 | 6/2018 | Evans et al. |
| 2018/0207005 A1 | 7/2018 | Chen et al. |
| 2018/0221177 A1 | 8/2018 | Kaltenbach et al. |
| 2018/0256365 A1 | 9/2018 | Bai |

(56) References Cited

U.S. PATENT DOCUMENTS

| | | |
|---|---|---|
| 2018/0256366 A1 | 9/2018 | Bai |
| 2018/0263791 A1 | 9/2018 | Bai |
| 2018/0296368 A1 | 10/2018 | Gill |
| 2018/0303633 A1 | 10/2018 | Yi |
| 2019/0091040 A1 | 3/2019 | Gill |
| 2019/0209345 A1 | 7/2019 | LaChappelle |
| 2019/0216618 A1 | 7/2019 | Gill |
| 2019/0343660 A1 | 11/2019 | Gill |
| 2019/0380846 A1 | 12/2019 | Lipsey et al. |
| 2020/0054466 A1 | 2/2020 | Gill et al. |
| 2020/0197193 A1 | 6/2020 | Byrne et al. |
| 2020/0268532 A1 | 8/2020 | Meijer et al. |

FOREIGN PATENT DOCUMENTS

| | | |
|---|---|---|
| CN | 106994694 | 8/2017 |
| DE | 309 367 | 11/1918 |
| DE | 319 092 | 2/1920 |
| DE | 323 970 | 8/1920 |
| DE | 24 34 834 | 2/1976 |
| DE | 26 07 499 | 9/1977 |
| DE | 198 54 762 | 6/2000 |
| DE | 101 05 814 | 9/2002 |
| DE | 203 15 575 | 1/2004 |
| DE | 698 16 848 | 4/2004 |
| DE | 10 2012 009 699 | 11/2013 |
| DE | 10 2017 005 761 | 2/2020 |
| DE | 10 2017 005 762 | 2/2020 |
| DE | 10 2017 005 764 | 2/2020 |
| DE | 10 2017 005 765 | 2/2020 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 617 103 | 1/2006 |
| EP | 1 557 547 | 1/2011 |
| EP | 2 532 927 | 12/2012 |
| EP | 2 612 619 | 7/2013 |
| EP | 2 616 017 | 7/2013 |
| EP | 2 653 137 | 10/2013 |
| EP | 2 664 302 | 11/2013 |
| EP | 2 719 361 | 4/2014 |
| EP | 2 114 315 | 5/2016 |
| EP | 2 890 333 | 12/2016 |
| EP | 2 978 389 | 5/2017 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 357 725 A | 7/2001 |
| GB | D 3023680 | 4/2006 |
| GB | 2 444 679 | 6/2008 |
| JP | 53-011456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| JP | 2018-167375 | 11/2018 |
| WO | WO 95/024875 | 9/1995 |
| WO | WO 96/023643 | 8/1996 |
| WO | WO 99/021517 | 5/1999 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044052 | 4/2008 |
| WO | WO 2008/044207 | 4/2008 |
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2013/038143 | 3/2013 |
| WO | WO 2014/027897 | 2/2014 |
| WO | WO 2015/120076 | 8/2015 |
| WO | WO 2015/120083 | 8/2015 |
| WO | WO 2015/128604 | 9/2015 |
| WO | WO 2016/051138 | 4/2016 |
| WO | WO 2017/061879 | 4/2017 |
| WO | WO 2017/084637 | 5/2017 |
| WO | WO 2017/199127 | 11/2017 |
| WO | WO 2017/212128 | 12/2017 |
| WO | WO 2018/006722 | 1/2018 |
| WO | WO 2018/054945 | 3/2018 |
| WO | WO 2018/056799 | 3/2018 |
| WO | WO 2018/096188 | 5/2018 |
| WO | WO 2018/121983 | 7/2018 |
| WO | WO 2018/130428 | 7/2018 |
| WO | WO 2018/132711 | 7/2018 |
| WO | WO 2018/158554 | 9/2018 |
| WO | WO 2018/178420 | 10/2018 |
| WO | WO 2018/180782 | 10/2018 |
| WO | WO 2018/218129 | 11/2018 |
| WO | WO 2020/208557 | 10/2020 |
| WO | WO 2020/234777 | 11/2020 |

OTHER PUBLICATIONS

Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.

Bellman et al., "SPARKy 3: Design of an Active Robotic Ankle Prosthesis with Two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale, AZ, pp. 511-516.

Belter et al., "Mechanical Design and Performance Specifications of Anthropomorphic Prosthetic Hands: A Review", JRRD, Jan. 2013, vol. 50, No. 5, pp. 599-618.

Biddiss et al., "Consumer Design Priorities for Upper Limb Prosthetics", Disability and Rehabilitation: Assistive Technology, Nov. 2007, vol. 2, No. 6, pp. 346-357.

Biddiss et al., "Upper Limb Prosthesis Use and Abandonment: A Survey of the Last 25 Years", Prosthetics and Orthotics International, Sep. 2007, vol. 31, No. 3, pp. 236-257.

Biddiss et al., "Upper-Limb Prosthetics: Critical Factors in Device Abandonment", American Journal of Physical Medicine & Rehabilitation, Dec. 2007, vol. 86, No. 12, pp. 977-987.

(56) References Cited

OTHER PUBLICATIONS

Chicoine et al., "Prosthesis-Guided Training of Pattern Recognition-Controlled Myoelectric Prosthesis", in Proceedings of the 34th Annual International Conference of the IEEE EMBS, San Diego, CA, Aug. 28-Sep. 1, 2012, pp. 1876-1879.
Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.
Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.
Controzzi et al., "Miniaturized Non-Back-Drivable Mechanism for Robotic Applications", Mechanism and Machine Theory, Oct. 2010, vol. 45, No. 10, pp. 1395-1406.
Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.
"DC Circuit Theory", https://www.electronics-tutorials.ws/dccircuits/dcp_1.h5ml, Date verified by the Wayback Machine Apr. 23, 2013, pp. 16.
Dechev et al., "Multiple Finger, Passive Adaptive Grasp Prosthetic Hand", Mechanism and Machine Theory, Oct. 1, 2001, vol. 36, No. 10, pp. 1157-1173.
Dellorto, Danielle, "Bionic Hands Controlled by iPhone App", CNN, Apr. 12, 2013, pp. 4 http://www.cnn.com/2013/04/12/health/bionic-hands.
Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.
Fougner et al., "Control of Upper Limb Prostheses: Terminology and Proportional Myoelectric Control-A Review", IEEE Transactions on Neural Systems Rehabilitation Engineering, Sep. 2012, vol. 20, No. 5, pp. 663-677.
Fukuda et al., "Training of Grasping Motion Using a Virtual Prosthetic Control System", 2010 IEEE International Conference on Systems Man and Cybernetics (SMC), Oct. 10-13, 2010, pp. 1793-1798.
Gaine et al., "Upper Limb Traumatic Amputees. Review of Prosthetic Use", The Journal of Hand Surgery, Feb. 1997, vol. 22B, No. 1, pp. 73-76.
Grip Chips™, Datasheet, May 15, 2014, Issue 1, http://touchbionics.com/sites/default/files/files/Grip%20Chip%20datasheet%20May%202014.pdf, pp. 1.
Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-091008-11.
Jebsen et al., "An Objective and Standardized Test of Hand Function", Archives of Physical Medicine and Rehabilitation, Jun. 1969, vol. 50, No. 6, pp. 311-319.
Johannes et al., "An Overview of the Developmental Process for the Modular Prosthetic Limb," John Hopkins APL Technical Digest, 2011, vol. 30, No. 3, pp. 207-216.
Kermani et al., "Friction Identification and Compensation in Robotic Manipulators", IEEE Transactions on Instrumentation and Measurement, Dec. 2007, vol. 56, No. 6, pp. 2346-2353.
Kuiken et al., "Targeted Muscle Reinnervation for Real-Time Myoelectric Control of Multifunction Artificial Arms", JAMA, Feb. 11, 2009, vol. 301, No. 6, pp. 619-628.
Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.
Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.

Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.
Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.
Maxon Precision Motors, Inc., "Maxon Flat Motor: EX 10 flat 10 mm, brushless, 0.25 Watt", Specification, May 2011, p. 181.
Maxon Precision Motors, Inc., "Maxon EC Motor: EC10 10 mm, brushless, 8 Watt", Specification, May 2011, p. 140.
Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.
Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.
Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.
Press Release, "Touch Bionics Introduce Digitally Controlled Supra Wrist", http://www.touchbionics.com/news-events/news/touch-bionics-introduce-digitally-controlled-supra-wrist, May 3, 2016 in 2 pages.
Raspopovic et al., "Restoring Natural Sensory Feedback in Real-Time Bidirectional Hand Prostheses", Science Translational Medicine, Feb. 5, 2014, vol. 6, No. 222, pp. 1-10.
Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.
Sensinger, "Efficiency of High-Sensitivity Gear Trains, such as Cycloid Drives", Journal of Mechanical Design, Jul. 2013, vol. 135, No. 7, pp. 071006-1-071006-9.
Sensinger et al., "Exterior vs. Interior Rotors in Robotic Brushless Motors", 2011 IEEE International Conference on Robotics and Automation (ICRA), Shanghai, China, May 9-13, 2011, pp. 2764-2770.
Sensinger, "Selecting Motors for Robots Using Biomimetic Trajectories: Optimum Benchmarks, Windings, and other Considerations," 2010 IEEE International Conference on Robotics and Automation (ICRA), Anchorage, AL, USA, May 3-8, 2010, pp. 4175-4181.
Sensinger, "Unified Approach to Cycloid Drive Profile, Stress, and Efficiency Optimization", Journal of Mechanical Design, Feb. 2010, vol. 132, pp. 024503-1-024503-5.
Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.
Stix, Gary, "Phantom Touch: Imbuing a Prosthesis with Manual Dexterity", Scientific American, Oct. 1998, pp. 41 & 44.
Sutton et al., "Towards a Universal Coupler Design for Modern Powered Prostheses", MEC 11 Raising the Standard, Proceedings of the 2011 MyoElectric Controls/Powered Prosthetics Symposium Frederiction, New Brunswick, Canada, Aug. 14-19, 2011, pp. 5.
Tan et al., "A Neural Interface Provides Long-Term Stable Natural Touch Perception", Science Translational Medicine, Oct. 8, 2014, vol. 6, No. 257, pp. 1-11.
Tang, "General Concepts of Wrist Biomechanics and a View from Other Species", The Journal of Hand Surgery, European Volume, Aug. 2008, vol. 33, No. 4, pp. 519-525.
"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.
Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.

(56) References Cited

OTHER PUBLICATIONS

Vilarino, Martin, "A Novel Wireless Controller for Switching among Modes for an Upper-Limb Prosthesis", The Academy TODAY, Jan. 2014, vol. 10, No. 1, pp. A-12 to A-15.
Wettels et al., "Grip Control Using Biomimetic Tactile Sensing Systems", IEEE/ASME Transactions on Mechatronics, Dec. 2009, vol. 14, No. 6, pp. 718-723.
Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.
International Search Report and Written Opinion in Application No. PCT/IB2018/060072, dated May 14, 2019.
Invitation to Pay Additional Fees in Application No. PCT/IB2018/060072, dated Mar. 22, 2019.
"Supro Wrist", Touch Bionics, https://web.archive.org/web/20160928141440/http://www.touchbionics.com/products/supro-wrist as archived Sep. 28, 2016 in 3 pages.
Touch Bionics PowerPoint Presentation in 3 pages, believed to be shown at ISPO Conference in Leipzig, Germany, May 2016.
Touch Bionics PowerPoint Slide in 1 page, believed to be presented at Advanced Arm Dynamics company Jan. 11, 2016.
Touch Bionics Screenshots of video in PowerPoint Presentation in 4 pages, believed to be shown at ISPO Conference in Leipzig, Germany, May 2016.
International Preliminary Report on Patentability and Written Opinion in Application No. PCT/IB2018/060072, dated Jun. 25, 2020.
Childress et al., "Control of Limb Prostheses", American Academy of Orthopaedic Surgeons, Mar. 2004, Chapter 12, pp. 173-195.
Connolly, "Prosthetic Hands from Touch Bionics", Industrial Robot, Emerald Group Publishing Limited, Jun. 2008, vol. 35, No. 4, pp. 290-293.
"DuPont Engineering Design—The Review of DuPont Engineering Polymers in Action", http://www.engpolymer.co.kr/x_data/magazine/engdesign07_2e.pdf, Feb. 2007, pp. 16.
Heckathorne, Craig W., "Components for Electric-Powered Systems", American Academy of Orthopaedic Surgeons, Mar. 2004, Chapter 11, pp. 145-171.
Hojjat et al., "A Comprehensive Study on Capabilities and Limitations of Roller-Screw with Emphasis on Slip Tendency", Mechanism and Machine Theory, Oct. 2009, vol. 44, No. 10, pp. 1887-1899.
Kent et al., "Electromyogram Synergy Control of a Dexterous Artificial Hand to Unscrew and Screw Objects", Journal of Neuroengineering and Rehabilitation, Mar. 2014, vol. 11, No. 1, pp. 1-20.
Kyberd et al., "Two-Degree-of-Freedom Powered Prosthetic Wrist", Journal of Rehabilitation Research & Development, Jul. 2011, vol. 48, No. 6, pp. 609-617.
Majd et al., "A Continuous Friction Model for Servo Systems with Stiction", in Proceedings of the IEEE Conference on Control Applications, Sep. 28-29, 1995, pp. 296-301.
Miller et al., "Summary and Recommendations of the Academy's State of the Science Conference on Upper Limb Prosthetic Outcome Measures", Journal of Prosthetics Orthotics, Oct. 2009, vol. 21, pp. 83-89.
Osborn et al., "Utilizing Tactile Feedback for Biomimetic Grasping Control in Upper Limb Prostheses", Department of Biomedical Engineering, Johns Hopkins University, Baltimore, USA, Nov. 5, 2013, pp. 4.
Pedrocchi et al., "MUNDUS Project: Multimodal Neuroprosthesis for Daily Upper Limb Support", Journal of Neuroengineering and Rehabilitation, Jul. 2013, vol. 10, No. 66, pp. 20.
Pinzur et al., "Functional Outcome Following Traumatic Upper Limb Amputation and Prosthetic Limb Fitting", The Journal of Hand Surgery, Sep. 1994. vol. 19, pp. 836-839.
Resnik et al., "The DEKA Arm: Its Features, Functionality, and Evolution During the Veterans Affairs Study to Optimize the DEKA Arm", Prosthetics and Orthotics International, Oct. 2013, vol. 38, No. 6, pp. 492-504.

Scheme et al., "Electromyogram Pattern Recognition for Control of Powered Upper-Limb Prostheses: State of the Art and Challenges for Clinical Use", Journal of Rehabilitation Research & Development (JRRD), Jul. 2011, vol. 48, No. 6, pp. 643-659.
Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.
Toledo et al., "A Comparison of Direct and Pattern Recognition Control for a Two Degree-of-Freedom Above Elbow Virtual Prosthesis", in Proceedings 34th Annual International Conference of the IEEE EMBS, Aug. 2012, pp. 4332-4335.
Weir et al., "Design of Artificial Arms and Hands for Prosthetic Applications", Biomedical Engineering and Design Handbook, Jul. 2009, vol. 2, pp. 537-598.
Whiteside et al., "Practice Analysis Task Force: Practice Analysis of the Disciplines of Orthotics and Prosthetics", American Board for Certification in Orthotics and Prosthetics, Inc., 2000, pp. 1-51.
Zampagni et al., "A Protocol for Clinical Evaluation of the Carrying Angle of the Elbow by Anatomic Landmarks", Journal of Shoulder and Elbow Surgery, Jan. 1, 2008, vol. 17, No. 1, pp. 106-112.
9 Worm Gear Pair, KHK Technical Information, Oct. 21, 2008, pp. 291-299.
Baek et al., "Design and Control of a Robotic Finger for Prosthetic Hands", Proceedings of the 1999 IEEE International Conference on Intelligent Robots and Systems, pp. 113-117.
Bretthauer et al., "A New Adaptive Hand Prosthesis", Handchirurgie Mikrochirurgie Plastische Chirurgie, Feb. 2008, pp. 40-45.
Butterfaβ et al., "DLR-Hand II: Next Generation of a Dextrous Robot Hand", IEEE International Conference on Robotics and Automation, Seoul, Korea, May 21-26, 2001, vol. 1, pp. 109-114.
Edsinger-Gonzales, Aaron, "Design of a Compliant and Force Sensing Hand for a Humanoid Robor", 2005, pp. 5.
Ama, Excerpts from American Medical Association, Guides to the Evaluation of Permanent Impairment (5th ed. 2000), pp. 432-453.
Fildes, Jonathan, "Bionic Hand Wins Top Tech Prize", BBC News, Jun. 9, 2008, http://news.bbc.co.uk/2/hi/science/nature/7443866.stm, pp. 3.
Gaiser et al., "A New Anthropomorphic Robotic Hand", 2008 8th IEEE-RAS International Conference on Humanoid Robots, Dec. 1-3, 2008, Daejeon, Korea, pp. 418-422.
"iLimb Bionic Hand Now Ready for Marker", Technovelgy.com, www.technovelgy.com/ct/Science-Fiction-News.asp?NewsNum=1125, as printed Jul. 6, 2020 in 3 pages.
Kargov et al., "Applications of a Fluidic Artificial Hand in the Field of Rehabilitation", Rehabilitation Robotics, Ch. 15, Aug. 2007, pp. 261-286.
Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.
Kargov et al., "Modularly Designed Lightweight Anthropomorphic Robot Hand", 2006 IEEE International Conference on Multisensor Fusion and Integration for Intelligent Systems, Sep. 3-6, 2006, Heidelberg, Germany, pp. 155-159.
Kawasaki et al., "Design and Control of Five-Fingered Haptic Interface Opposite to Human Hand", IEEE Transactions on Robotics, Oct. 2007, vol. 23, No. 5., pp. 909-918.
Lotti et al., "UBH 3: A Biologically Inspired Robotic Hand", Jan. 2004, pp. 7.
MEC '05: Integrating Prosthetics and Medicine, University of New Brunswick's MyoElectric Controls/Powered Prosthetics Symposium, Aug. 17-19, 2005, Fredericton NB Canada, pp. 260.
"Motor Technology—Girard Gearboxes Low Backlash Principle Explained", Motor Technology, https://www.motec.co.uk/tip-gearbox_principle.htm as printed May 23, 2012 in 3 pages.
Poppe, Zytel HTN Provides a Helping Hand, DuPont Engineering Design 8 (2007), pp. 3.
Puig et al., "A Methodology for the Design of Robotic Hands with Multiple Fingers", International Journal of Advanced Robotic Systems, 2008, vol. 5, No. 2, pp. 177-184.

(56) References Cited

OTHER PUBLICATIONS

Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.
Schulz et al., "Die Entwicklung Einer Multifunktionalen Kosmetischen Handprothese", Prothetik, Orthopädie-Technik, Aug. 2006, pp. 627-632.
The Weir Thesis ("Weir Thesis") is entitled "An Externally-Powered, Myo-Electrically Controlled Synergetic Prosthetic Hand for the Partial-Hand Amputee", published Aug. 1989, pp. 365.
Ward, Derek Kempton, "Design of a Two Degree of Freedom Robotic Finger", Sep. 1996, pp. 155.
Weir et al., "A Myoelectrically Controlled Prosthetic Hand for Transmetacarpal Amputations", JPO Journal of Prosthetics and Orthotics, Jun. 2001, vol. 13, No. 2, pp. 26-31.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.

* cited by examiner

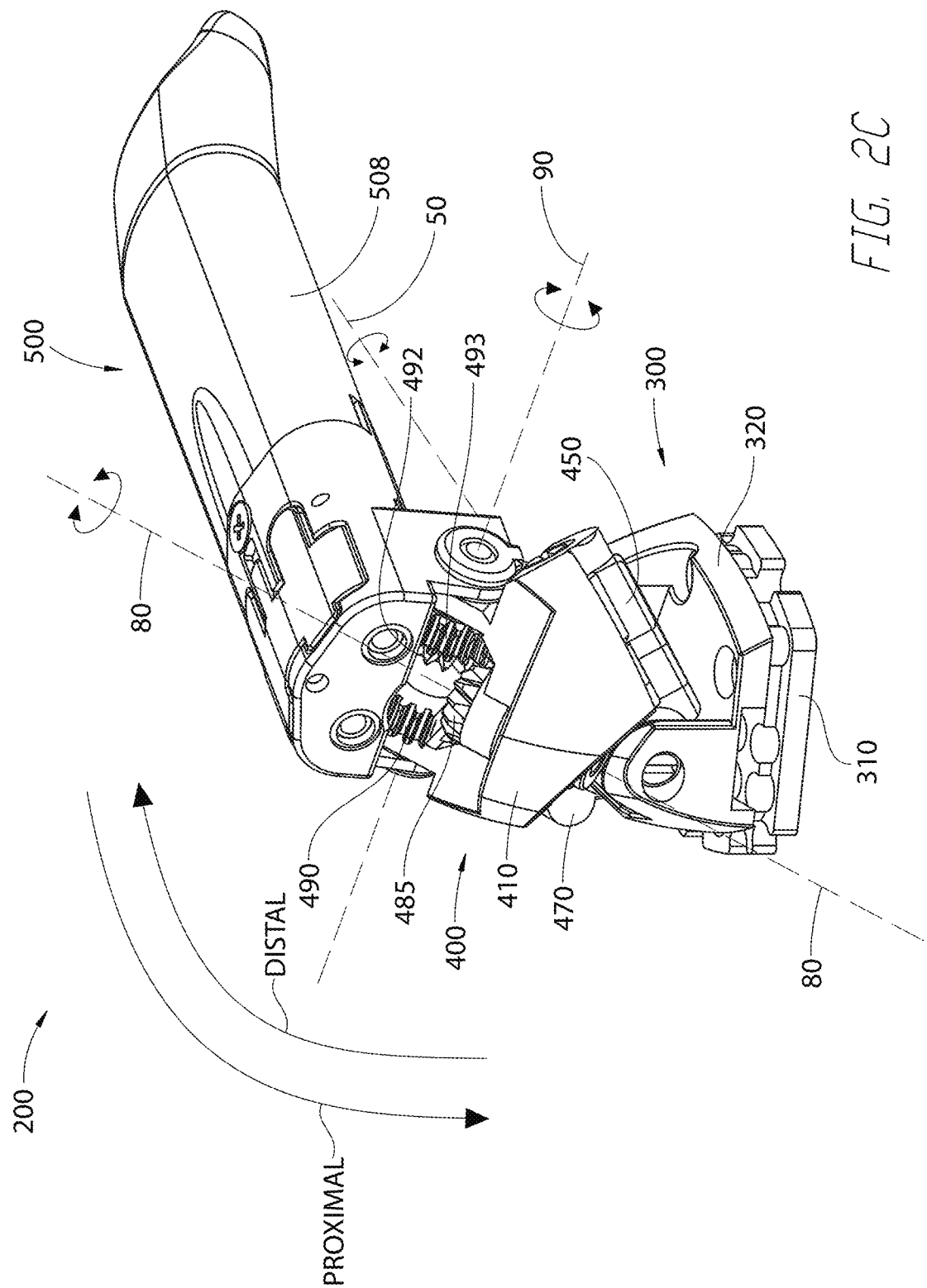

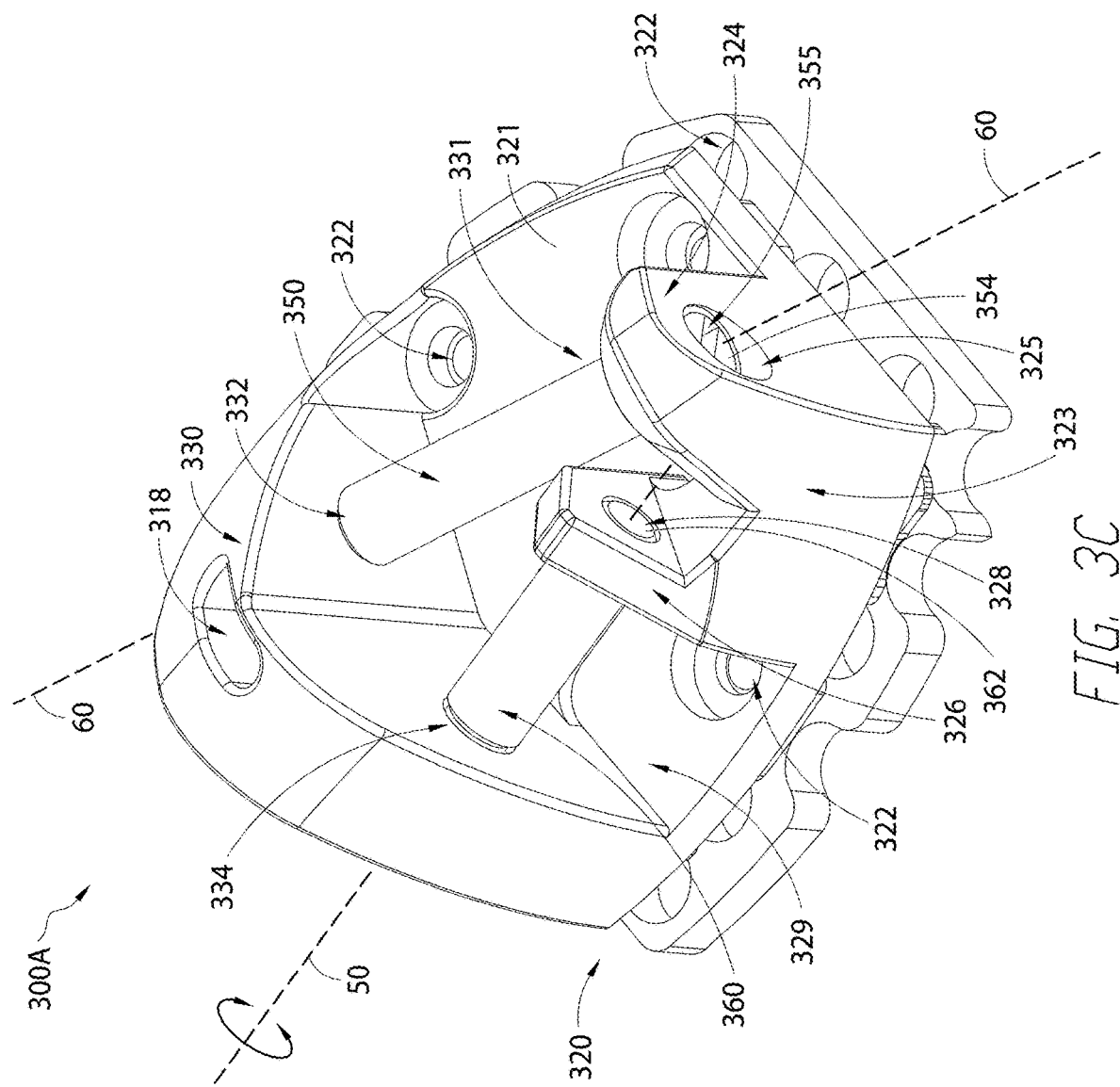

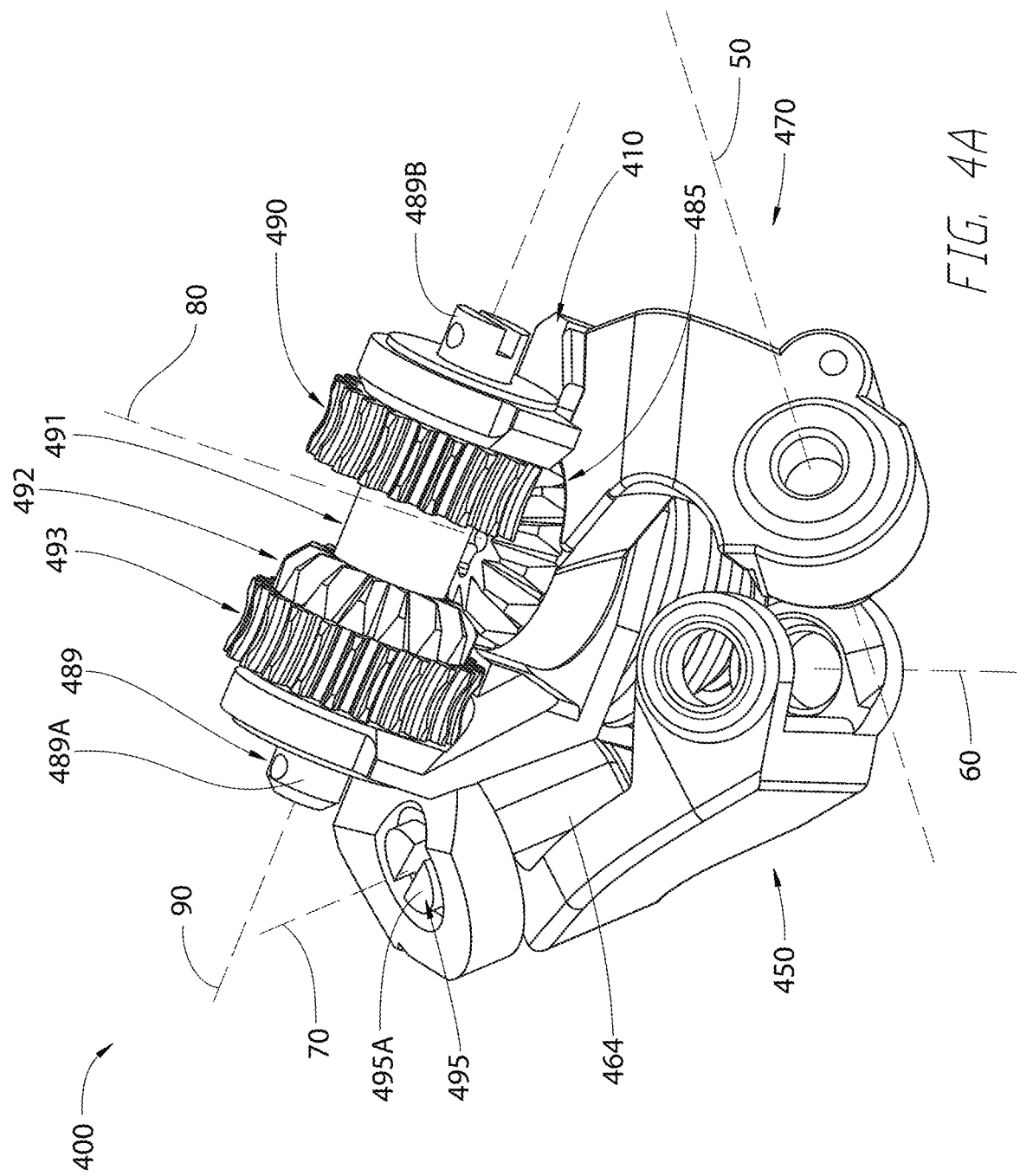

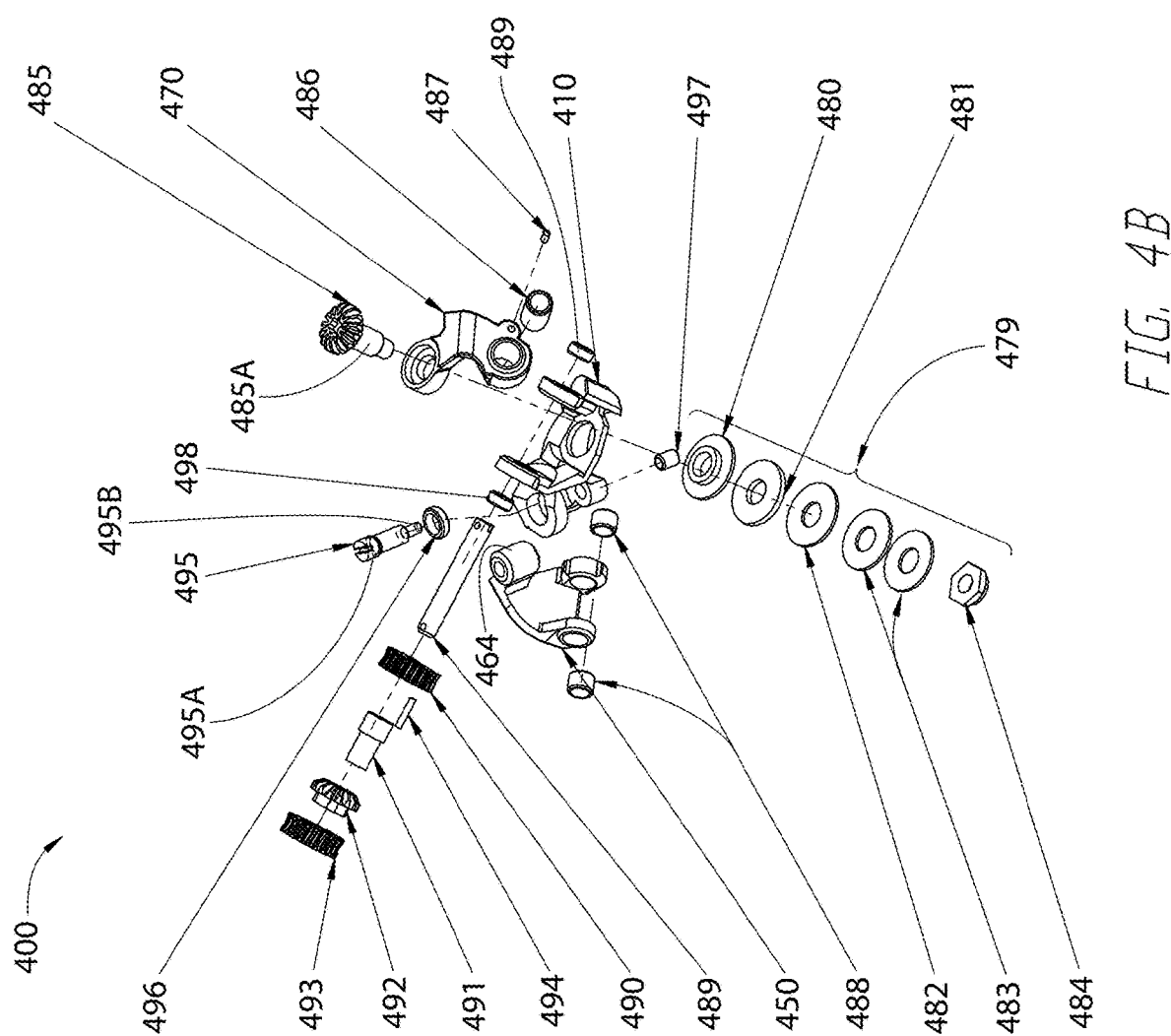

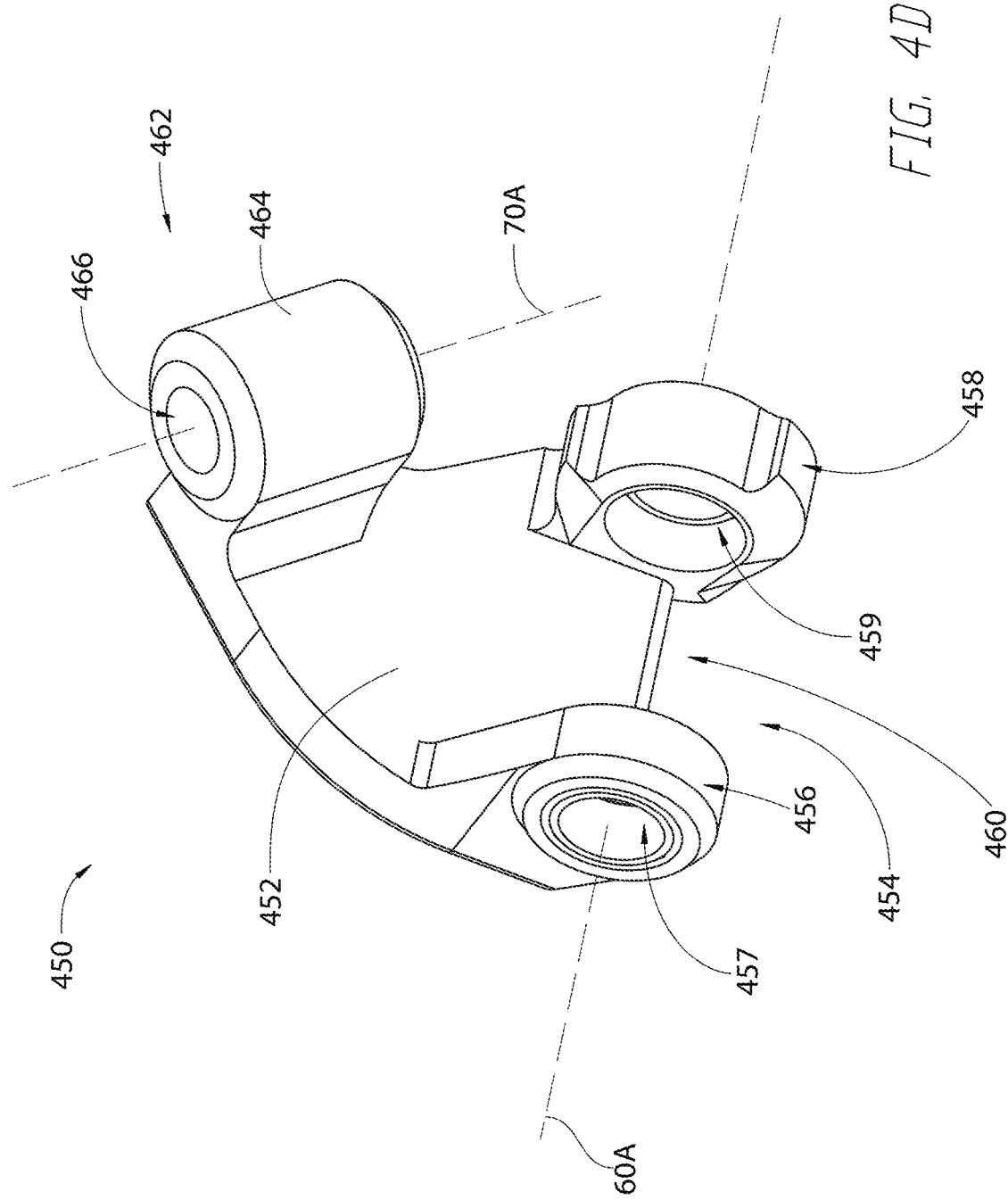

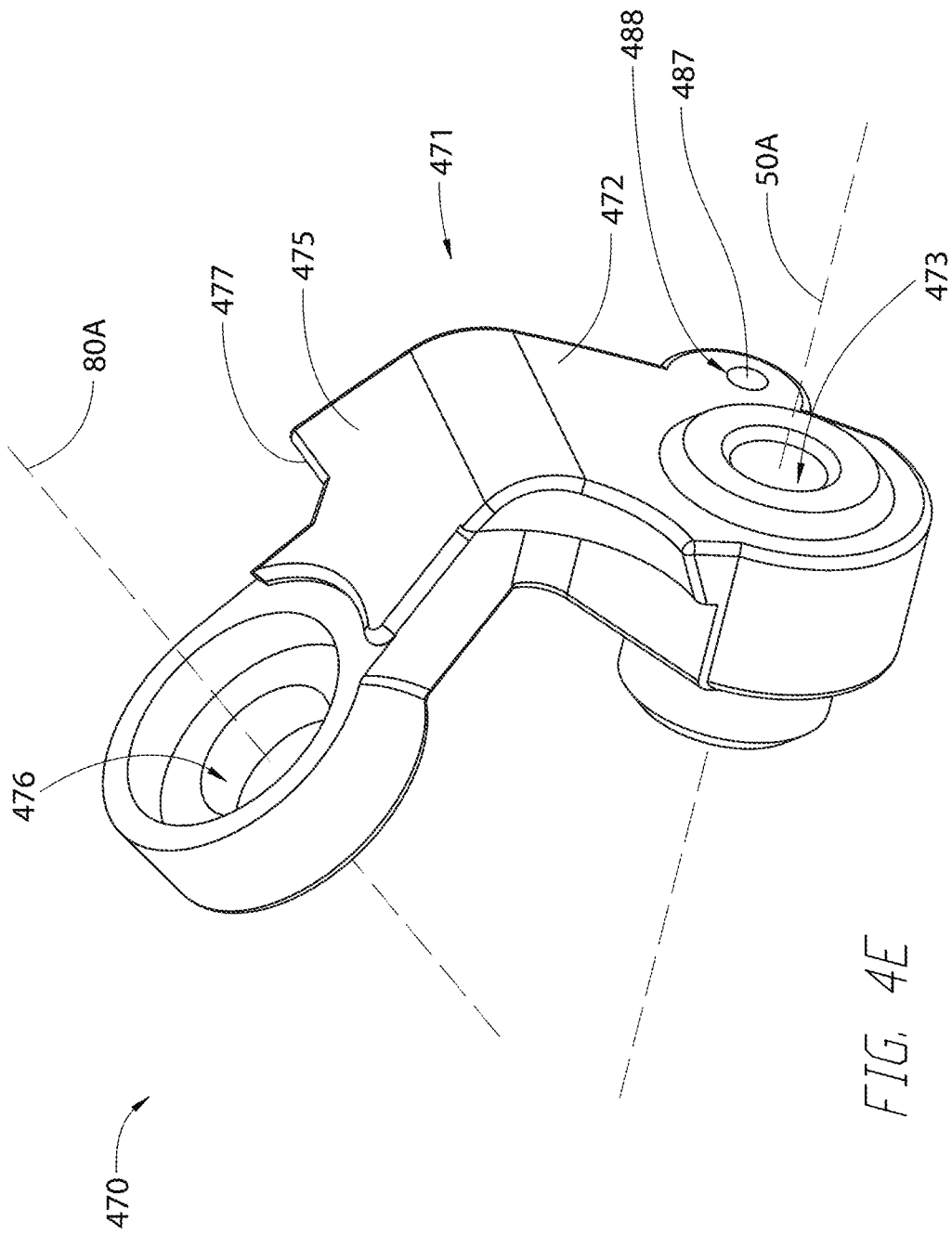

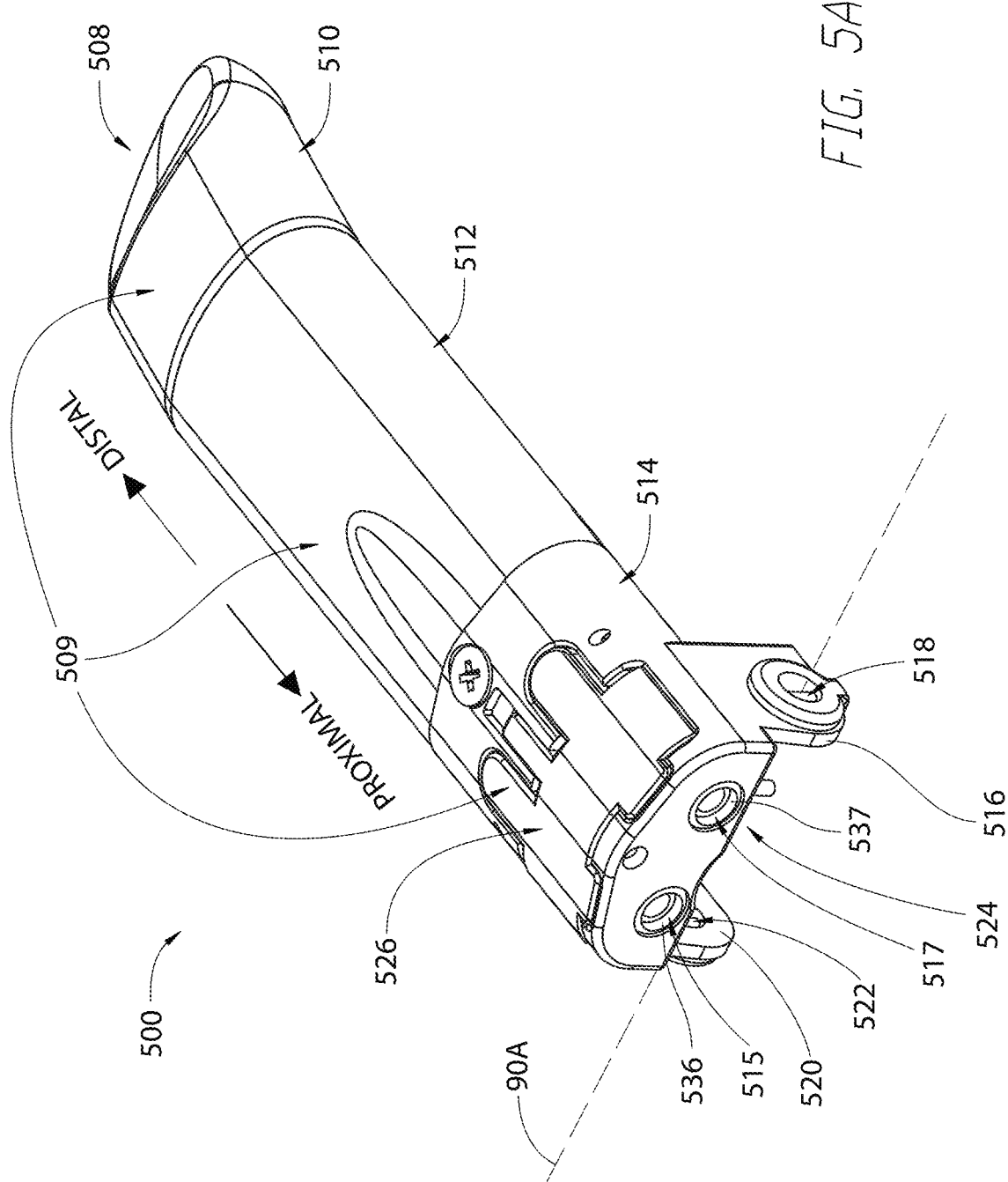

POWERED PROSTHETIC THUMB

CROSS-REFERENCE TO RELATED APPLICATIONS

The present application claims priority to U.S. Provisional Patent Application No. 62/599,559, titled "Powered Prosthetic Thumb" and filed on Dec. 15, 2017, which is incorporated herein by reference in its entirety for all purposes and forms a part of this specification.

BACKGROUND

Field

Features related to prosthetics are disclosed, in particular features related to a prosthetic thumb.

Description of the Related Art

A loss of a limb or part of a limb creates challenges for the amputee in performing simple tasks. The loss of upper limbs creates particular challenges due to the intricacy and dexterity of the human hand. Existing solutions for prosthetic digits provide limited movements. For example, existing digit prosthetics, such as prosthetic thumbs and fingers, do not provide in a natural manner the full range of motion and capabilities of a sound thumb. Improvements in this area are therefore desirable.

SUMMARY

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure. The embodiments disclosed herein each have several aspects no single one of which is solely responsible for the disclosure's desirable attributes.

Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods.

In a first aspect, a powered prosthetic thumb is described. The powered prosthetic thumb comprises a mount, a digit and an actuator. The digit is rotatably coupled with the mount about a first axis and a second axis, the first axis non-parallel with the second axis. The actuator is configured to cause rotation of the digit about the first axis. An orientation of the first axis relative to the mount changes as the digit rotates about the second axis.

Various embodiments of the various aspects may be implemented. The actuator may be configured to rotate in a first direction to cause the digit to rotate about the first axis. The powered prosthetic thumb may further comprise a second actuator configured to cause the digit to rotate about the second axis. An orientation of the first axis relative to the second axis may change as the digit rotates about the second axis. The first axis may rotate about the second axis as the digit rotates about the second axis. The powered prosthetic thumb may further comprise a clutch assembly configured to allow for manual rotation of the digit about the second axis. The powered prosthetic thumb may further comprise a first worm wheel and a first worm gear in mechanical communication with the first worm wheel, where the actuator is configured to cause rotation of the digit about the first axis by causing rotation of the first worm gear. The powered prosthetic thumb may further comprise a first bevel gear and a second bevel gear in mechanical communication with the first bevel gear, where the second actuator is configured to cause rotation of the digit about the second axis by causing rotation of the first bevel gear. The powered prosthetic thumb may further comprise a chassis rotatably coupling the mount with the digit. The powered prosthetic thumb may further comprise a first link and a second link, with each link rotatably coupling the chassis with the mount. The first axis may be a pinch axis, such that rotation of the digit about the first axis causes the digit to open or close, and the second axis may be a lateral axis, such that rotation of the digit about the second axis causes lateral rotation of the digit. The digit may comprise the first actuator. The mount may be configured to couple with a prosthetic socket mounted on a residual limb. The mount may be configured to couple with a partial prosthetic hand. The mount may be configured to couple with an upper limb. The upper limb may be a prosthetic arm or natural arm.

In another aspect, a powered prosthetic thumb is described. The powered prosthetic thumb comprises a mount, a digit, an actuator and a clutch. The digit is rotatably connected to the mount at least about a first axis. The actuator is in mechanical communication with the digit and configured to rotate the digit about the first axis. The clutch is coupled with the mount and the digit, with the clutch providing a rotational resistance to the digit about the first axis. The digit is configured to be operated in a manual mode wherein the rotational resistance is overcome to allow the digit to be manually rotated about the first axis.

Various embodiments of the various aspects may be implemented. The clutch assembly may comprise a compression spring. The compression spring may comprise a Belleville washer. The digit may be rotatably coupled with the mount about the first axis and a second axis, where the first axis is non-parallel with the second axis. A orientation of the second axis relative to the mount may change as the digit rotates about the first axis. The clutch may provide the rotational resistance to the digit about the first axis via a bevel gear. The bevel gear may be configured to rotate in response to overcoming the rotational resistance to allow the digit to be manually rotated about the first axis.

In another aspect, a powered prosthetic thumb is described. The powered prosthetic thumb comprises a lower assembly, a middle assembly, an upper assembly, a first actuator and a second actuator. The lower assembly comprises a mount. The middle assembly comprises a chassis, where the middle assembly is rotatably coupled with the lower assembly about a lateral axis. The upper assembly comprises a digit, where the upper assembly is rotatably coupled with the middle assembly about a pinch axis. The first actuator is configured to cause rotation of the digit relative to the chassis about the pinch axis. The second actuator is configured to cause rotation of the digit about the lateral axis by causing rotation of the chassis relative to the mount about the lateral axis. The pinch axis is configured to rotate about the lateral axis as the digit rotates about the lateral axis.

Various embodiments of the various aspects may be implemented. The lateral axis may extend along a first direction, the pinch axis may extend along a second direction that is non-parallel with respect to the first direction, and the second actuator may be configured to cause rotation of the chassis relative to the mount about the lateral axis such that the second direction remains non-parallel to the first direction. The lateral axis may not intersect the pinch axis while the chassis rotates about the lateral axis. A proximal portion of the mount may be positioned proximal to a distal portion of the chassis, a proximal portion of the chassis may be positioned proximal to a distal portion of the digit, and the lateral axis may be positioned proximal to the digit. The lateral axis may be positioned proximal to the chassis. The pinch axis may be positioned distal to the proximal portion of the chassis. The digit may be configured to rotate about the pinch axis in a first plane that comprises the lateral axis.

In another aspect, a powered prosthetic thumb is described. The powered prosthetic thumb comprises a lower assembly, a middle assembly and an upper assembly. The lower assembly comprises a mount configured to attach to a prosthetic hand. The mount may attach, for example, to a socket or other portion of the hand or arm. The middle assembly is coupled with the lower assembly. The middle assembly comprises a chassis, a first link having a first end rotatably connected to the mount and a second end connected to the chassis, a second link having a first end rotatably connected to the mount and a second end rotatably connected to the chassis, a shaft connected to the chassis along a pinch axis and having disposed thereon a first worm wheel, a second worm wheel and a first bevel gear, and a second bevel gear connected to the chassis and in mechanical communication with the first bevel gear. The upper assembly is coupled with the middle assembly. The upper assembly comprises a digit extending along a longitudinal axis, a first actuator configured to rotate a first worm gear about a first axis parallel with the longitudinal axis, the first worm gear in mechanical communication with the first worm wheel, and a second actuator configured to rotate a second worm gear about a second axis parallel with the longitudinal axis, the second worm gear in mechanical communication with the second worm wheel. Actuating the first actuator causes the digit to rotate about the pinch axis. Actuating the second actuator causes the digit to rotate about a lateral axis, that is not parallel with the pinch axis, due to mechanical communication between the first bevel gear and the second bevel gear.

Other aspects include other embodiments of a prosthetic thumb, methods of operating a prosthetic thumb, and other prostheses that may or may not include a prosthetic thumb as described herein. Prosthetic digits other than a thumb may incorporate features described herein.

BRIEF DESCRIPTION OF THE DRAWINGS

FIGS. 2A-2C are various perspective views of the thumb of FIGS. 1A and 1B having a lower, middle and upper assembly.

FIGS. 3C and 3D are perspective and exploded views respectively of another embodiment of a lower assembly that may be used with the thumb of FIGS. 1A and 1B.

FIGS. 4A and 4B are perspective and exploded views respectively of the middle assembly of FIGS. 2A-2C having a rocker, coupler and a swaying chassis.

FIG. 4D is a perspective view of the rocker of FIGS. 4A-4B.

FIG. 4E is a perspective view of the coupler of FIGS. 4A-4B.

FIGS. 5A and 5B are perspective views of the upper assembly of FIGS. 2A-2C.

DETAILED DESCRIPTION

Figure 1A:
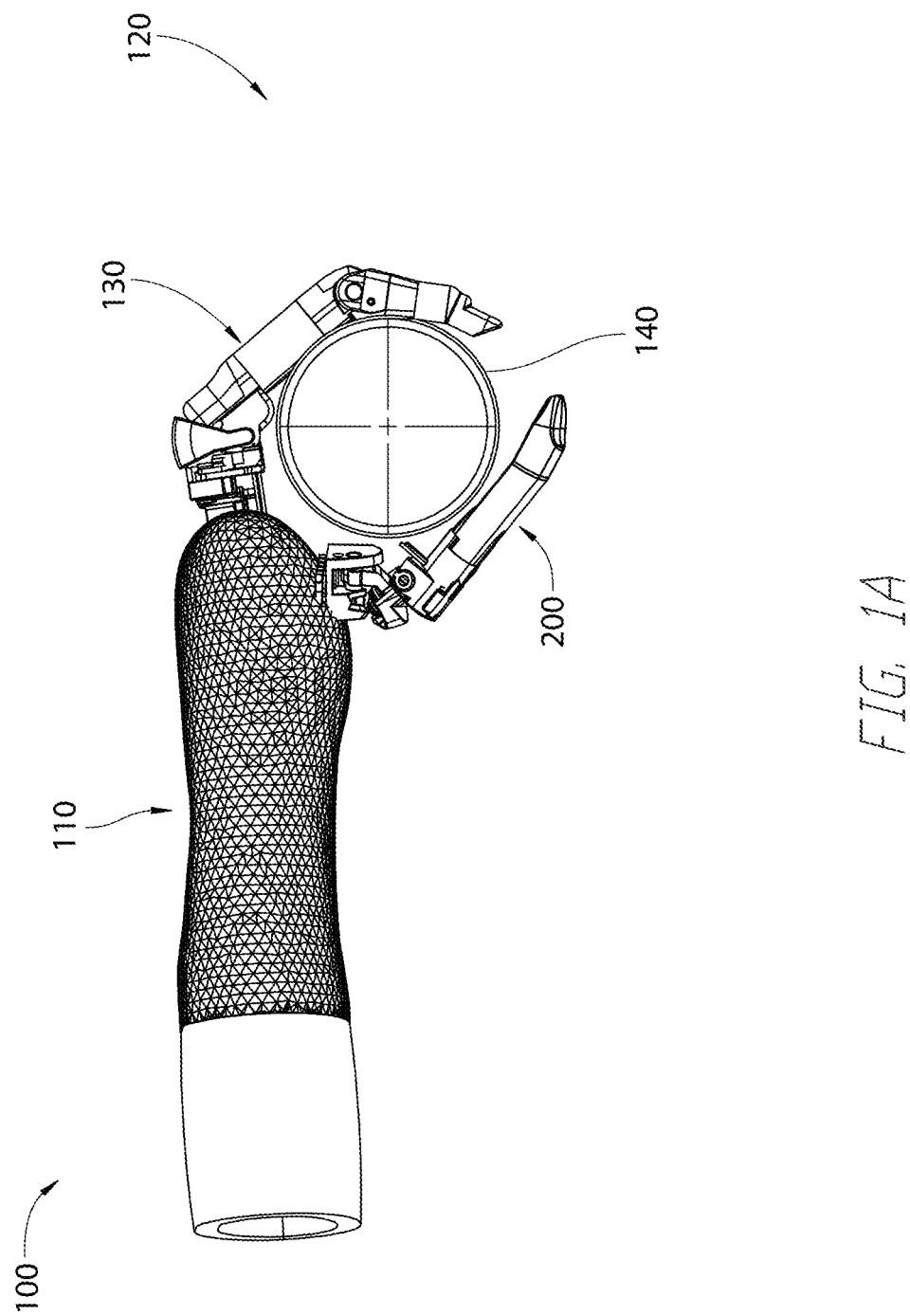
FIGS. 1A and 1B are side and front views respectively of embodiments of an upper limb that include an embodiment of a powered prosthetic thumb.
Figure 1B:
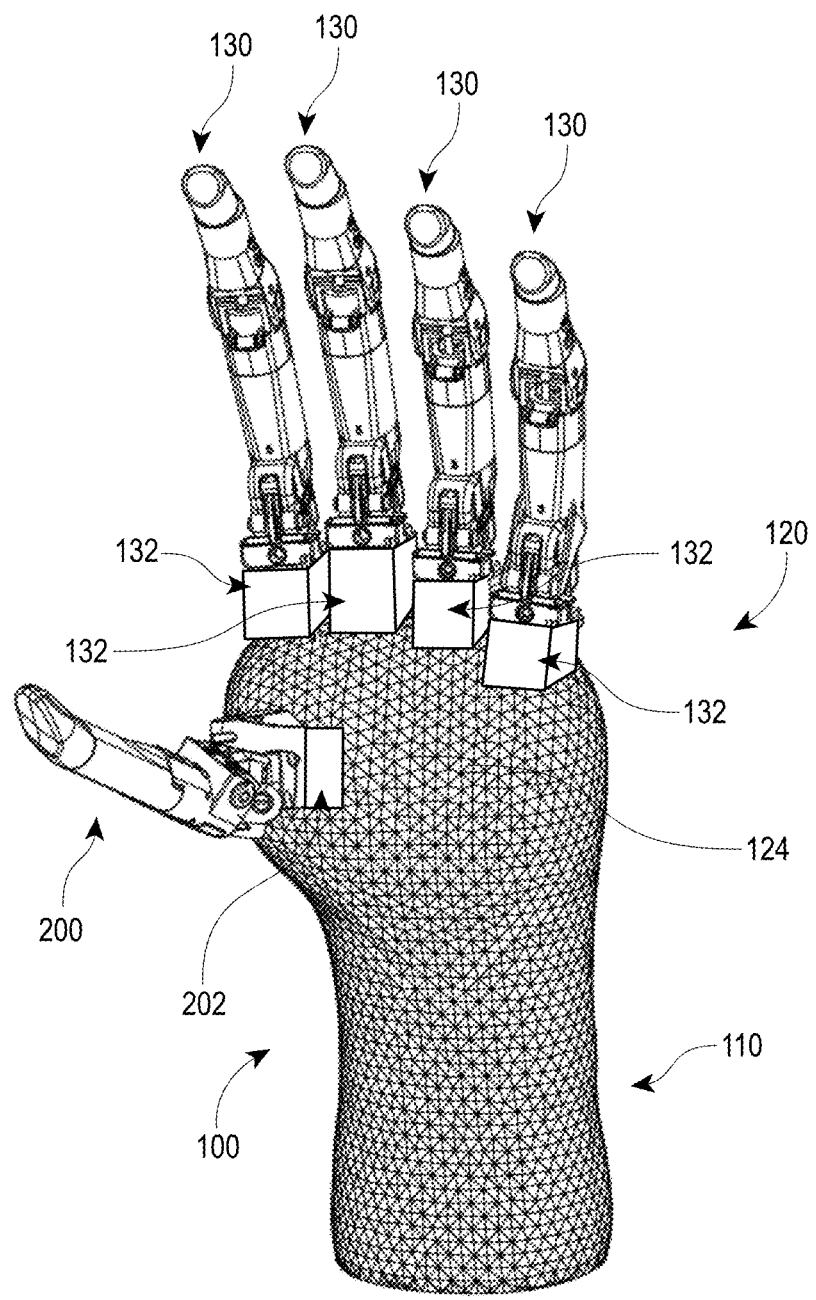

FIGS. 1A and 1B are side and front views respectively of an embodiment of an upper limb 100 that includes an embodiment of a powered prosthetic thumb 200. As shown, the upper limb 100 may include an arm 110 attached to a hand 120. The arm 110 may be a prosthetic arm. The hand 120 may be a left hand. The thumb 200 may also be used with a right hand. In some embodiments, the arm 110 may be a natural arm, i.e. a natural or sound human arm. The arm 110 may be a stump and/or include a fitting on a distal end thereof. The arm 110 may be or include one or more prosthetic sockets 132 and/or 202 (see FIG. 1B) mounted on the arm 110, such as a residual limb, or on the hand 120, such as a palm portion 124 (see FIG. 1B) on the end of the arm 110. For clarity the prosthetic sockets 132, 202 are not shown in FIG. 1A. The prosthetic sockets 132 may connect one or more finger digits 130 with the arm 110 and/or the palm 124. The prosthetic socket 202 may connect the thumb 200 with the arm 110 and/or the palm 124. The prosthetic sockets 132, 202 may be a variety of different types of suitable prosthetic sockets. For example, the prosthetic sockets 132, 202 may be created by a prosthetist for the appropriate anatomical spacing and location of the finger digits 130 and the thumb 200 relative to the end of the arm 110 or relative to the palm 124 of the hand 120. The prosthetic sockets 132, 202 are shown schematically in FIG. 1B.

The hand 120 may be a prosthetic hand, for example a full prosthetic hand or a partial prosthetic hand. The hand 120 may include one or more prosthetic finger digits 130, for example the four finger digits 130 and the thumb 200. In some embodiments, there may be fewer than four of the digits 130, for example where the hand 120 is a partial prosthetic hand. The thumb 200 may be used with partial hand patients, for example that are missing a natural thumb only, and who could thus use the thumb 200 with a partial hand system. In some embodiments, the thumb 200 may be used with patients that are missing a natural thumb and/or one or more natural fingers and/or a natural palm, either partially or completely missing any of these natural anatomical body parts. In some embodiments, the digits 130 and/or thumb 200 may connect directly with the arm 110.

Thus the hand 120 may just include the digits 130 and/or just the thumb 200. An example embodiment of a partial prosthetic hand 120A that the thumb 200 may be used with is shown and described with respect to FIGS. 8A and 8B. There may be a structure, such as a palm structure, of the palm 124 attaching the digits 130 and/or thumb 200 with the arm 110. In some embodiments, there may just be the thumb 200 attached to a partial prosthetic hand 120, which is attached to a natural partial hand having one or more natural fingers, which is attached to a natural arm 110.

The digits 130 and the thumb 200 may be configured to facilitate grasping an object 140. As shown in FIG. 1A, the object 140 may be a cylinder, or other objects. The thumb 200 described herein facilitates grasping and/or manipulating this and other objects by allowing for movement in a natural manner and through large ranges of motion, for example by providing rotation about multiple axes, simultaneous rotation about multiple axes, rotation about one or more moving axes, among other advantages, as further described.

Figure 2A:
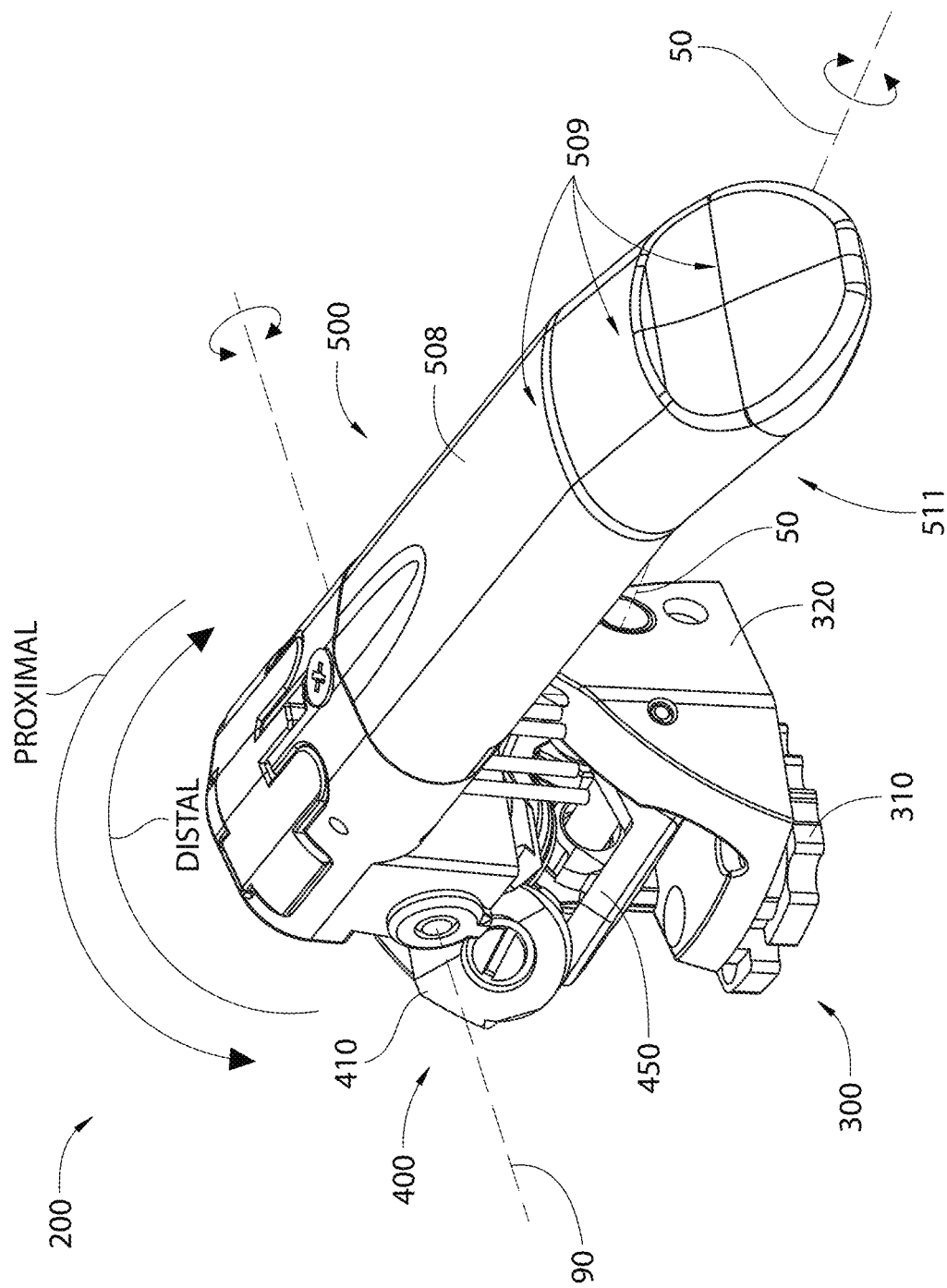
Figure 2B:
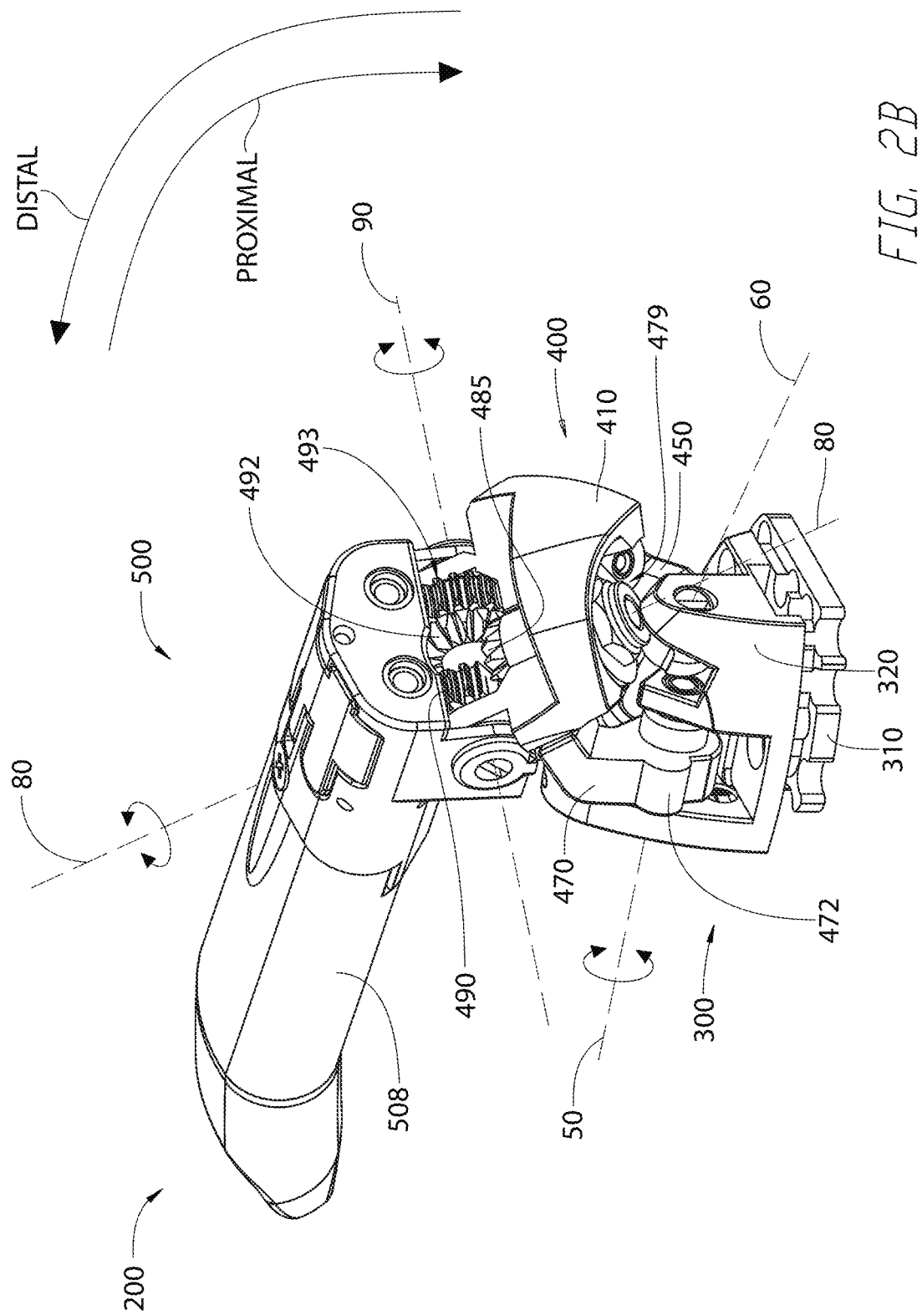

FIGS. 2A-2C are various perspective views of the thumb 200. As shown, the thumb 200 may include a lower assembly 300, a middle assembly 400 and an upper assembly 500. The lower assembly 300 may be configured to attach to the hand 120, for example a palm structure thereof, or to the arm 110. In some embodiments, the lower assembly 300 attaches to a full prosthetic hand 120 or a partial prosthetic hand 120. The lower assembly 300 may include a plate 310 for attaching to the hand 120. The thumb 200 may provide rotation of the upper assembly 500 about a pinch axis 90, about a lateral axis 50, or about both the pinch axis 90 and the lateral axis 50, as further described below. Other rotations and movements may also be performed by the thumb 200. For example, the thumb 200 may include other joints along the upper assembly 500 that rotate as well. The upper assembly 500 or portions thereof may be considered a digit, such as a thumb digit, which performs the various rotations, as further described herein. A cover 508 may extend along the digit. The digit may have a top side 509 and an opposite underside 511. The underside 511 may refer to a side of the digit that would be on the same side of a palm of a sound hand. The top side 509 may refer to a side of the digit that would be on the same side as the back of a sound hand.

The assemblies 300, 400, 500 may have rotatable connections with each other, as generally described here, and as described in further detail herein, for example with respect to FIGS. 3A-5C. Various geometric references may be used to describe the thumb 200. As shown, a distal direction extends in a direction generally from the lower assembly 300 toward the upper assembly 500. A proximal direction extends generally in a direction from the upper assembly 500 toward the lower assembly 300.

The lower assembly 300 is rotatably connected with the middle assembly 400. The middle assembly 400 may include a rocker 450 and a coupler 470. Proximal ends of the rocker 450 and the coupler 470 may be rotatable connected with a mount 320 of the lower assembly 300. The middle assembly 400 may include a swaying chassis 410 rotatably connected with a distal end of the rocker 450 and connected with the coupler 470. The upper assembly 500 is rotatably connected at a proximal end thereof with the middle assembly 400. The upper assembly 500 may include a cover 508 having a proximal end rotatably connecting the upper assembly 500 with a distal end of the swaying chassis 410.

The upper assembly 500 is configured to rotate about a pinch axis 90 and/or a lateral axis 50, as described in further detail herein. The pinch axis 90 may be defined and be fixed with respect to portions of the upper assembly 500. Further, the upper assembly 500 may move in directions other than merely rotating about the pinch axis 90. Thus, the orientation of the pinch axis 90 may also change, for example relative to the lower assembly 300 such as the mount 320, due to movement of the upper assembly 500. The upper assembly may rotate about the pinch axis 90 due to mechanical communication between various worm gears 534, 542 and worm wheels 490, 493, as further described.

The lateral axis 50 may be defined and be fixed with respect to portions of the lower assembly 300. Further, the upper assembly 500 may move in directions other than merely rotating about the pinch axis 90. Thus, the orientation of the pinch axis 90 may also change, for example relative to the lower assembly 300 such as the mount 320, due to movement of the upper assembly 500. The upper assembly 500 may rotate only about the pinch axis 90, only about the lateral axis 50, or about the pinch axis 90 and the lateral axis 50 simultaneously, as further described. The upper assembly 500 may rotate about the lateral axis 50 due to mechanical communication between a first bevel gear 492 and a second bevel gear 485, as further described. A clutch assembly 479 may allow for manual rotation of the upper assembly 500 about the lateral axis 50, for example to prevent damage in case of excessive force applied to the digit, as further described.

Figure 2E:
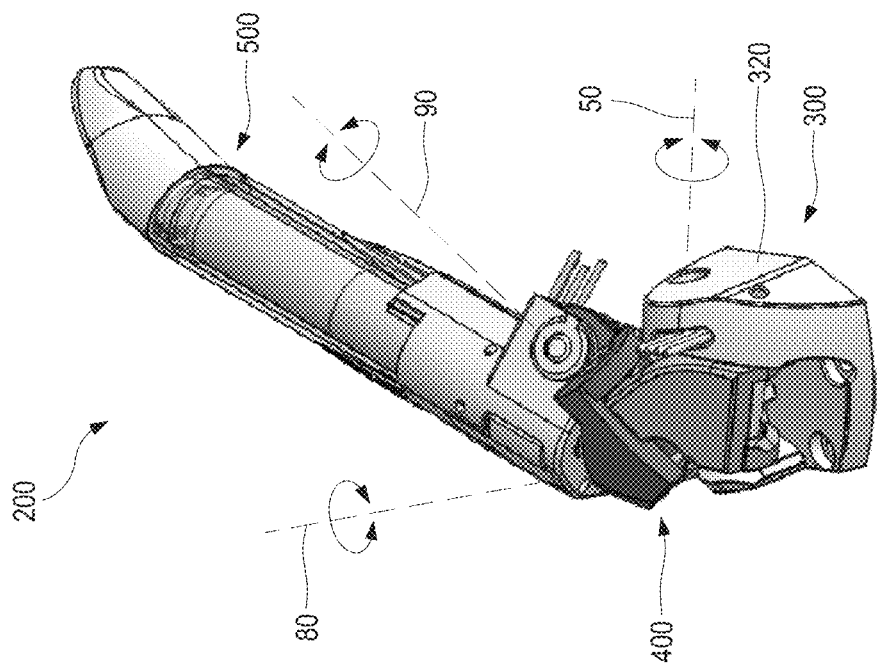
FIGS. 2D-2E are sequential perspective views of the thumb of FIGS. 1A and 1B showing sequential positions before and after, respectively, lateral rotation about a lateral axis.
Figure 2D:
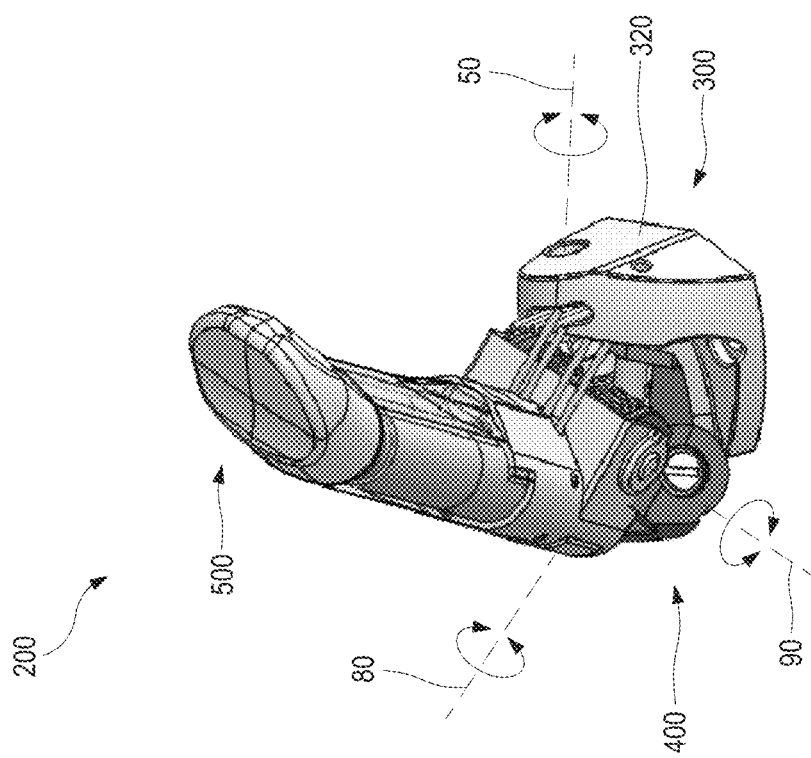

FIGS. 2D-2E are sequential perspective views of the thumb 200 showing sequential positions of the upper assembly 500 and other components before and after, respectively, lateral rotation about the lateral axis 50. The upper assembly 500 has been rotated from the position in FIG. 2D to the position shown in FIG. 2E. Further, the orientation of the 1 pinch axis 90 in FIG. 2E have changed relative to the orientation in FIG. 2D. The change in orientation of the axis 90 may be described as relative to the lateral axis 50, the mount 320 or other fixed reference portion of the thumb 200. Thus the pinch axis 90 may rotate about the lateral axis 50. The upper assembly 500 may rotate back from the position shown in FIG. 2E to the position shown in FIG. 2D. Under manual lateral rotation, a clutch component may rotate about the clutch axis 80 to allow for lateral manual rotation, as further described. These are just example positions meant to illustrate one possible rotation about the lateral axis 50. In some embodiments, the thumb 200 may be configured such that the lateral axis 50 moves as the upper assembly 500 performs the various rotations described herein.

In some embodiments, rotation of the upper assembly 500 may be described with respect to a rotation vector. It is understood in the art that a rotation vector has a magnitude that is proportional to the amount or speed of rotation and a direction that is perpendicular to the plane of rotation. It is also understood in the art that a rotation vector's magnitude and direction may be described by three components corresponding to coordinates of three mutually orthogonal axes, such as a reference X-Y-Z axis system. Here, a reference axis system may be fixed with respect to a fixed portion of the thumb, such as the lower assembly 300, for example the mount 320. A reference axis system may instead be fixed to the upper assembly 500 and move with the upper assembly 500 as the upper assembly 500 moves. A rotation vector of the upper assembly 500 may be described with respect to such reference frames. In some embodiments, the upper assembly 500 may have a rotation vector that has one, two or three components in such reference frame that are non-zero. For example, the upper assembly 500 may rotate about both the lateral axis 50 and the pinch axis 90 simultaneously. As further example, the upper assembly 500 may rotate about only the lateral axis 50. In these and other instances, the corresponding rotation vector of the upper assembly 500 may have multiple components that are non-zero. In some embodiments, the rotation vector of the upper assembly 500 may change magnitude and/or direction as the upper assembly rotates.

In some embodiments, rotation of the upper assembly 500 may be described with respect to Euler angles. As is understood in the art, Euler angles are three angles that describe the orientation of a body with reference to a fixed reference frame. In some embodiments, a fixed reference frame may be as described above, for example an X-Y-Z axis system fixed with respect to the mount 320. The upper assembly 500 may have a local reference frame that moves with the upper assembly 500. In some embodiments, Euler angles may describe the relationship between a final orientation of the upper assembly 500 relative to an initial orientation, by describing the angular rotations of the local reference frame relative to the fixed reference frame. In some embodiments, rotation of the upper assembly 500 may be described with one, two or three non-zero Euler angles. For example, the upper assembly 500 may rotate about both the lateral axis 50 and the pinch axis 90 simultaneously. As further example, the upper assembly 500 may rotate about only the lateral axis 50. In these and other instances, the relative orientation between a starting orientation of the upper assembly 500 prior to rotating and a final orientation after rotating may be described with one, two or three Euler angles that are non-zero.

Figure 3A:
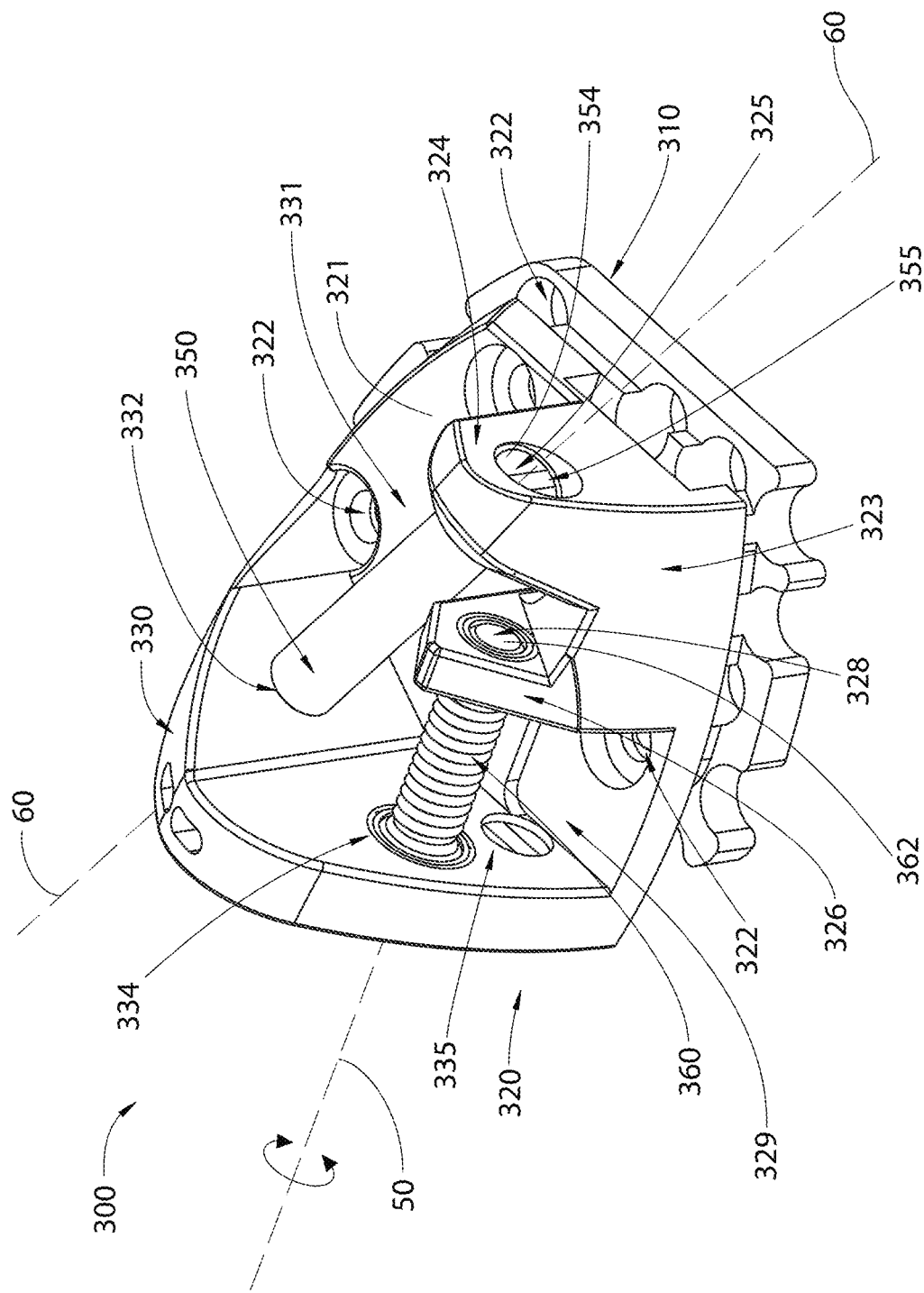
FIGS. 3A and 3B are perspective and exploded views respectively of the lower assembly of FIGS. 2A-2C.
Figure 3B:
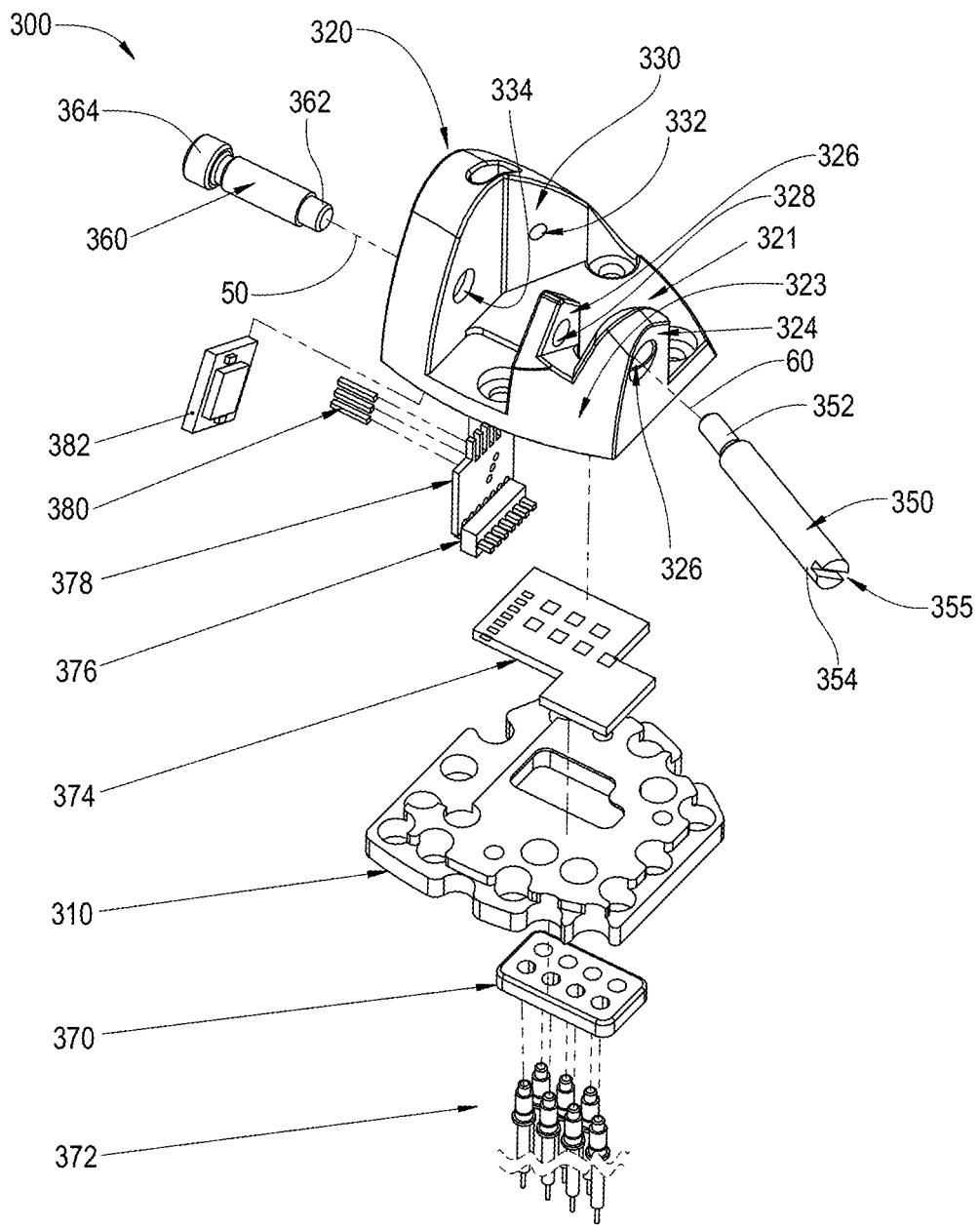

FIGS. 3A-3B show the lower assembly 300 in isolation from the remaining parts of the thumb 200. FIG. 3B is an exploded view of the lower assembly 300. As shown in the figures, the lower assembly 300 may include a plate 310. The plate 310 may be configured to attach to the hand 120. For example, the plate 310 may be attached on a first side thereof to the prosthetic hand 120, e.g. in a location where a sound thumb would be located. The plate 310 may be attached on an opposite second side thereof to a mount 320. The plate 310 may attach to the hand 120 and/or mount 320 with fasteners, other mechanical attachments, adhesives, other suitable attachment means, or combinations thereof.

The mount 320 may be a structural component configured to attach to the plate 310 and/or other structure and to attach, for example rotatably attach, to various parts of the middle assembly 400. The mount 320 may include a base 321. The base 321 provides a structural foundation for the mount 320. The base 321 may include one or more holes 322 extending therethrough. As shown there may be three holes 322. The holes 322 may receive a fastener, for example a screw, therethrough to attach the base 321 with the plate 310.

The mount 320 may include a first projection 323. The first projection 323 may provide attachment points for various components of the middle assembly 400. The first projection may be a raised portion of the mount 320 extending distally from the mount 320. The first projection 323 may include a first ear 324 and/or a second ear 326. The first and second ears 324, 326 may be projections extending distally from the first projection 323. The first ear 324 may include an opening 325 extending therethrough. The opening 325 may extend along and may align with a rocker axis 60. The opening 325 may define the rocker axis 60. The rocker axis 60 may align with an axis of rotation for various components of the middle assembly 400, such as a proximal portion of the rocker 450 as further described. The second ear 326 may include an opening 328 extending therethrough. The opening 328 may extend along and align with and/or define a lateral axis 50. The lateral axis 50 may align with an axis of rotation for various components of the middle assembly 400, such as a proximal portion of the coupler 470, as further described.

The mount 320 may include a second projection 330 extending distally from the mount 320 and spaced from the first projection 323. The second projection 330 may be laterally spaced from the first projection 323 to define one or more spaces therebetween. The second projection 330 may provide attachment points for various components of the middle assembly 400. The second projection 330 may include an opening 332 extending therethrough. The opening 332 may extend along and align with the rocker axis 60. The opening 332 may define the rocker axis 60. The opening 332 may therefore align or generally align with the opening 325. The portion of the second projection 330 having the opening 332 may be spaced from the portion of the first ear 324 having the opening 325 to define a space 331 therebetween. The second projection 330 may include an opening 334 extending therethrough. The opening 334 may align with the lateral axis 50. The opening 334 may define the lateral axis 50. The opening 334 may therefore align or generally align with the opening 328. The portion of the second projection 330 having the opening 334 may be spaced from the portion of the second ear 326 having the opening 328 to define a space 329 therebetween.

The lower assembly 300 may include a rocker pivot shaft 350. The shaft 350 may include a first end 352 and an opposite second end 354. The shaft may be an elongated structural element extending from the first end 352 to the second end 354. The shaft 350 may be located in the space 331 and received into the opening 332 and the opening 325. The first end 352 of the shaft 350 may be received by the opening 332, and the second end 354 may be received by the opening 325. The second end 354 may include a notch 355, for example a flat recess as shown. The notch 355 may allow for receiving a tool therein to adjust, for example rotate, the shaft 350. The shaft 350 may be aligned with, for example extend along, the rocker axis 60. The shaft 350 may provide a structural support for rotating the rocker 450 about the rocker axis 60, as further described. The shaft 350 may be rotatably stationary about the axis 60. In some embodiments, the shaft 350 may be configured to allow for rotation about the axis 60.

The lower assembly 300 may include a swaying chassis pivot shaft 360. The shaft 360 may include a first end 362 and an opposite second end 364. The shaft 360 may be an elongated structural element extending from the first end 362 to the second end 364. The shaft 360 may be located in the space 329 and received by the opening 328 and the opening 334. As shown the first end 362 may be received by the opening 328 and the second end 364 received by the opening 334. The shaft 360 may be threaded or not threaded. The shaft 360 may be aligned with, for example extend along, the lateral axis 50. The shaft 360 may provide a structural support for rotating the swaying chassis 410 about the lateral axis 50, as further described. The shaft 360 may be rotatably stationary about the lateral axis 50. In some embodiments, the shaft 360 may be configured to allow for rotation about the lateral axis 50.

The lower assembly 300 may include a pogo plate 370. The pogo plate 370 may receive one or more pogo pins 372. The lower assembly 300 may include a distribution circuit board 374. The pins 372 may establish a temporary connection between the circuit board 374 and other electronics of the thumb 200 and/or hand 120. This pins 372 may be slender cylinders containing two sharp, spring-loaded pins. The board 374 may be attached to the plate 310 and/or the mount 320. The board 374 may be in electrical communication with the pins 372. The pins 372 may actuate to establish the connection with the board 374. The board 374 may be in electrical communication with a circuit connection 376, such as a printed circuit board (PCB) connection. The circuit connection 376 may be on an actuator cable circuit board 378. The board 378 may include a series of circuit pins 380 which may be mounted to the circuit connection 376. The board 378 may be located inside the second projection 330 of the mount 320.

The lower assembly 300 may include a sensor 382. As shown the sensor 382 may be a Hall Effect sensor or Hall Effect sensor assembly. The sensor 382 may be a Hall Effect sensor assembly that senses one or more magnets of the thumb 200, as further described herein. The sensor 382 signals with different levels of current output depending on the proximity of a magnetic field. Thus a small magnet (e.g. about 0.5-5 mm diameter, preferably 1 mm or 2 mm diameter) may be positioned on one of the rotating links, such as the coupler 470, and as the link rotates the distance between the magnet and the sensor 382 changes. This in turn results in different values of current being signaled by the sensor 382. By calibrating the variation of the signaled current by the sensor 382 versus the associated angle that the thumb 200 or portions thereof such as the coupler 470 rotates, the signals may be read from the sensor 382 to determine the angular position of the thumb 200 or portions thereof, such as the coupler 470 and/or upper assembly 500. This data may be used to decide the next commands to the actuators to reduce or increase the angular position.

The sensor 382 may be located within the second projection 330. The sensor 382 may be positioned as an angle of 45 degrees or about 45 degrees. The sensor 382 may be positioned as an angle of 45 degrees or about 45 degrees relative to the base 321 and/or second projection 330. This positioning may account for outside effects such as the upper assembly 500 which may be metallic. As shown, the sensor 382 may be exposed through an opening 335 of the second projection 330. The sensor 382 may communicate with other components of the thumb 200 through the opening 335. For example, the sensor 382 may be a Hall Effect sensor assembly that communicates electromagnetically with one or more magnets, as further described herein.

The lower assembly 300 may be attached with the middle assembly 400, as further described. The shafts 350, 360 may provide rotational securements for various components of the thumb 200, as further described. As shown, the shaft 350 may be angled with respect to the shaft 360. The shaft 350 may be in a different plane than the shaft 360. The shaft 350 may be in a different plane and angled with respect to the shaft 360. The lateral axis 50 may be angled with respect to the axis 60. The lateral axis 50 may be in a different plane than the axis 60. The lateral axis 50 may be in a different plane and angled with respect to the axis 60. The shafts 350, 360 may align with respectively the axes 60, 50.

Figure 3D:
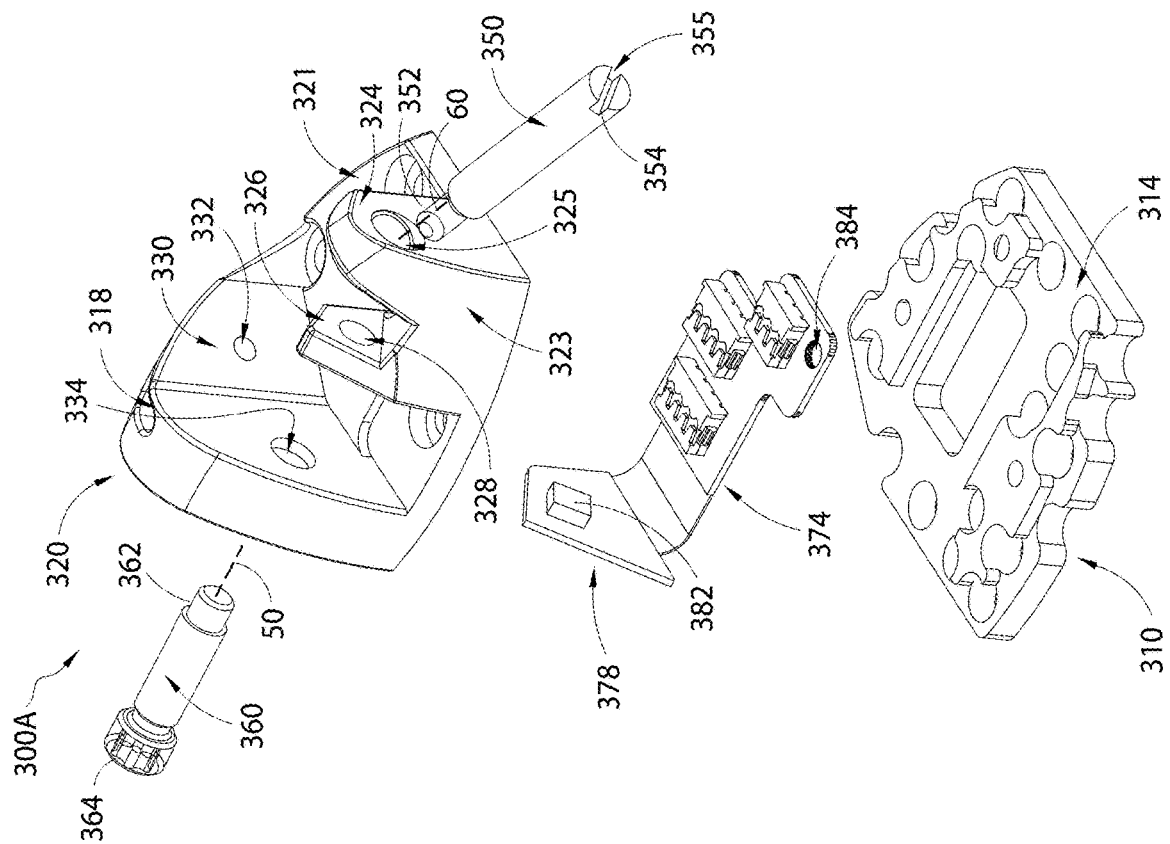

FIGS. 3C and 3D are perspective and exploded views respectively of another embodiment of a lower assembly 300A that may be used with the thumb 200. The lower assembly 300A may have the same or similar features and/or functions as the lower assembly 300. In addition or alternatively to the features described with respect to the lower assembly 300, the lower assembly 300A in some embodiments may include, for example, a plate 310 with a recess 314. As illustrated in FIG. 3D, the recess 314 may help provide the lower assembly 300A with a low profile and allow for minimal invasion. The recess 314 can allow components of the lower assembly 300A, such as the circuit board 374 and the plate 310, to fit together more tightly and create a lower overall profile on the thumb 200.

The thumb 200 may rotate and/or move quietly (e.g., without producing much noise) due to the compactness and design of the various rotating parts of the thumb 200. The thumb 200 may include at least one motor, such as the actuators 530, 538 described herein and shown in FIG. 5C. For example, the motor may be a brushed DC motor or a brushless motor. The motor may advantageously be very quiet. The mechanics of the motor(s) and the moving parts of the thumb 200 may be efficient. For example, the parts may be small and packed tightly as described herein and provide for quiet and smooth operation of the thumb during rotation about one or more of the rotational axes.

The lower assembly 300A may include at least one opening 318 in the mount 320. The opening 318 may be disposed on a top portion of the mount 320. In some embodiments, there may be more than one opening 318, such as with a dividing wall separating two or more openings 318. The opening 318 may extend downwardly through the second projection 330 to allow access to electrical connections between the circuit board 374 and electronics of the upper assembly 500 and/or other parts of the thumb 200. In some embodiments, the circuit board 374 may have a hole 384 configured to receive a fastener, such as a screw, to attach the circuit board 374 with other components of the lower assembly 300A.

Various components, such as the actuator cable circuit board 378 and/or the circuit board 374, may be separate components or may be included in a single component. For example, as shown in FIG. 3D, the circuit board 374 may include a flexible portion comprising the actuator cable circuit board 378. The board 378 may extend upwardly from the portion with the board 374. The board 378 may be received into the opening 318 of the mount 320 through a lower portion of the opening 318 in the bottom of the mount 320 for electrical connection. In some embodiments, components such as the pogo plate 370, pogo pins 372, circuit connection 376, and/or circuit pins 380 may not be included in the lower assembly 300A.

The lower assembly 300A may include a plug-in. The lower assembly 300A may not include the pogo plate 370 or pins 372 and instead have the plug-in. The plug-in may receive a standard type plug. The plug-in may be located for example on the bottom of the board 374. The design of the board 374 with the upward extending board 378 may allow for a more compact design that incorporates the plug-in and further contributes to the compactness of the electronics and to the overall thumb 200.

The lower assembly 300A may include one or more (e.g., 2 or 3) sensors 382. The sensor 382 may be coupled to the board 378. For example, the sensor 382 may be soldered to a surface, such as a back surface as shown and as oriented in FIG. 3D, of the board 378. Soldering the sensor 382 to the board 378 may reduce the number of parts in the lower assembly 300A. The use of fewer components may aid the reliability of the assembly 300A and simplify the manufacturing process. In some embodiments, the sensor 382 may be an analog Hall Effect sensor. The Hall Effect sensor may be used to obtain the absolute position of the thumb 200.

In some embodiments, a potentiometer may be used to obtain the absolute position of the thumb 200. In some embodiments, an incremental optical rotary encoder and/or gyro sensor may be used to control the thumb 200. For example, an incremental optical rotary encoder can generate a signal when the motor moves. The motor may include absolute optical encoders. For example, the motor may include absolute optical encoders which monitor the internal position of the motor. The position of the thumb 200 can be derived from the motor's rotation.

Figure 4C:
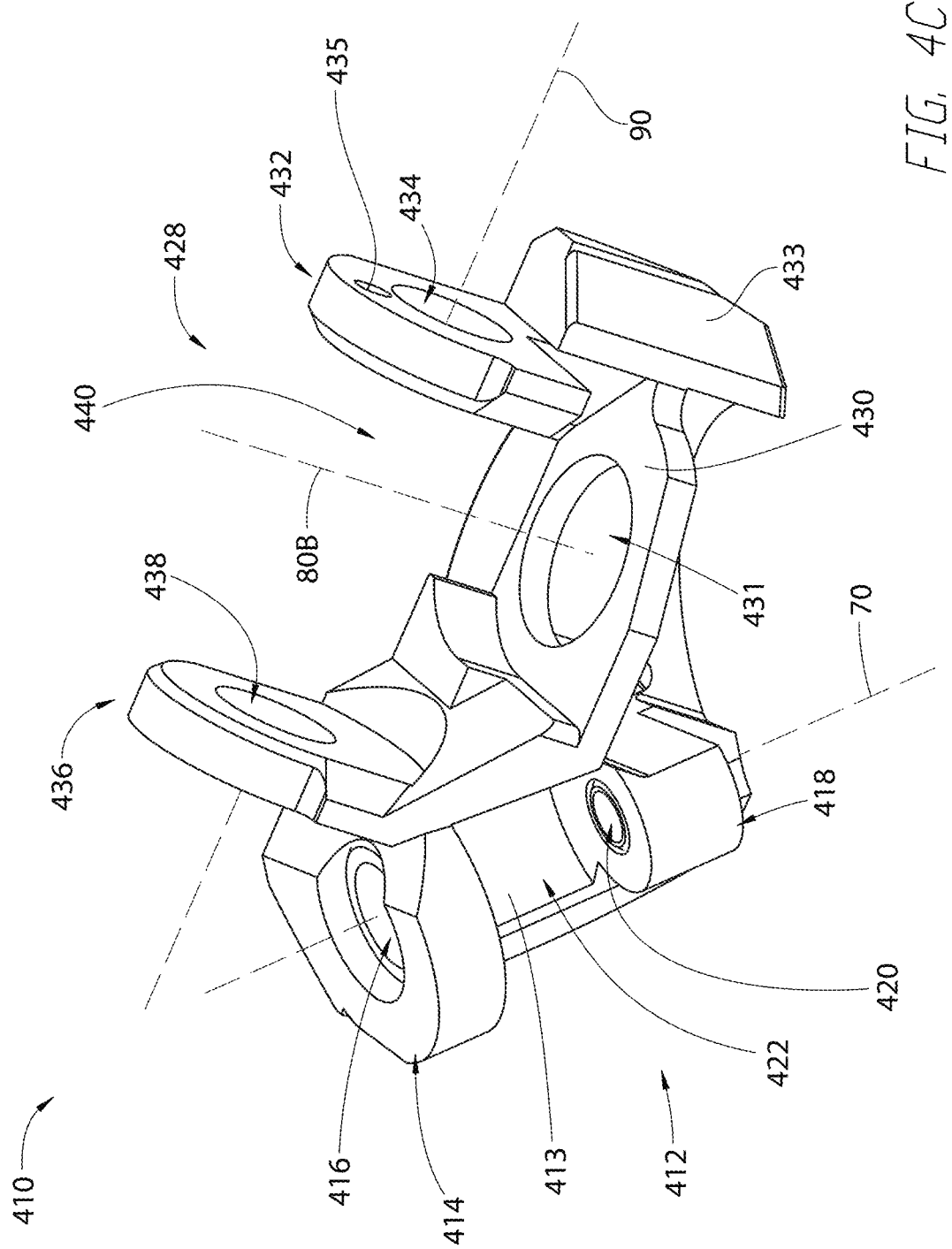
FIG. 4C is a perspective view of the swaying chassis of FIGS. 4A-4B.

FIG. 4A is a perspective view of the middle assembly 400. FIG. 4B is an exploded view of the middle assembly 400. As shown in the figures, the middle assembly 400 may include the swaying chassis 410, the rocker 450 and the coupler 470. FIG. 4C is a perspective view of the swaying chassis 410. FIG. 4D is a perspective view of the rocker 450. FIG. 4E is a perspective view of the coupler 470. The middle assembly 400 may couple with the lower assembly 300, as further described. As shown in FIG. 4A, a distal end of the rocker 450 may rotatably couple with the chassis 410 about a chassis axis 70. A distal end of the coupler 470 may couple with the chassis 410 about a clutch axis 80. The clutch axis 80 may be a rotation axis for a bevel gear to allow manual lateral rotation of the upper assembly 500, for example in case of excessive applied force to the digit, as further described. The distal end of the coupler 470 may be rotationally fixed with the chassis 410 about the clutch axis 80 to allow for automatic lateral rotation by the actuator, as further described herein.

As shown in FIG. 4C, the swaying chassis 410 may include a rocker attachment portion 412. The portion 412 may include a base 413 having a first ear 414 and a second ear 418 extending outwardly, for example perpendicularly, therefrom. The first and second ears 414, 418 may be spaced to define a rocker receiving space 422 therebetween. The first ear 414 may include an opening 416 extending therethrough. The second ear 418 may include an opening 420 extending therethrough. The openings 416, 420 may be aligned with and extend along or define the chassis axis 70. The portion 412 may rotatably couple the chassis 410 with the rocker 450 about the chassis axis 70, as further described.

The chassis 410 may include a coupler/upper assembly attachment portion 428. The portion 428 may be attached to or integral with the portion 412. The portion 428 may include a base 430. The base 430 may include an opening 431 extending therethrough. The opening 431 may be aligned with and extend along or define the lateral axis 50. The base 430 may include a first ear 432 and a second ear 436 extending outwardly, for example perpendicularly, therefrom. The first ear 432 and the second ear 436 may be spaced apart to define a main shaft receiving space 440 therebetween. The first ear 432 may include an opening 434 extending therethrough. The second ear 436 may include an opening 438 extending therethrough. The openings 434, 438 may be aligned with and extend along or define a pinch axis 90. The upper assembly 500 may rotate about the pinch axis 90 to open and close the digit, as further described.

The pinch axis 90 may be angled, for example perpendicular, with respect to the lateral axis 50. The axes 90, 50 may be oriented at other angles with respect to each other. The axes 90, 50 may or may not intersect. The chassis axis 70 may be angled with respect to the axes 50 and/or 90. The chassis axis 70 may be in a different plane than the axes 50 and/or 90. The digit may rotate about the axis 90 in a first plane. The first plane may move as the digit laterally rotates. The first plane may rotate about the axis 50 as the digit rotates laterally. In some embodiments, the axis 50 may intersect the first plane. In some embodiments, the axis 50 may in the first plane.

As shown in FIG. 4D, the rocker 450 may include a body 452. The body 452 may be a planar or generally planar structural support. The body 452 may include a first ear 456, a second ear 458 and/or a third ear 464. The ears 456, 458, 464 may be located on the same side of the body 452. The ears 456, 458, 464 may extend away from the body 452. The ears 456, 458, 464 may extend away from the body 452 in the same or generally the same direction.

The rocker 450 may include a proximal mount attachment portion 454. The portion 454 may include a proximal portion of the body 452 and the first ear 456 and the second ear 458. The first ear 456 may have an opening 457 extending therethrough. The second ear 458 may include an opening 459 extending therethrough. The openings 457, 459 may be aligned with and/or define a local axis 60A. The axis 60A may be aligned with the rocker axis 60, as further described, when the rocker 450 is assembled with the mount 320. The first ear 456 and the second ear 458 may be spaced apart from each other to define therebetween a shaft receiving space 460. The space 460 may receive therein the rocker pivot shaft 350 when the rocker 450 is assembled with the mount 320. When assembled, the proximal portion of the rocker 450 may rotate on the shaft 350 relative to the mount 320 and about the axis 60. There may be one or more bushings in the openings 457, 459.

The rocker 450 may include a distal chassis attachment portion 462. The chassis attachment portion 462 may be attached to or integral with the portion 454. The portion 462 may include a distal portion of the body 452 and the third ear 464. The ear 464 may include an opening 466 extending therethrough. The opening 466 may be aligned with and/or define a local chassis axis 70A. The local chassis axis 70A may align with the chassis axis 70 when the rocker 450 is assembled with the chassis 410. When assembled, the distal portion of the rocker 450 may rotate about the axis 70 relative to the chassis 470. There may be one or more bushings in the opening 466.

As shown in FIG. 4E, the coupler 470 may include a body 471. The body 471 may include a mount attachment portion 472 at a proximal end thereof. The portion 472 may include an opening 473 extending therethrough. The opening 473 may be aligned with and/or define a local axis 50A. The local axis 50A may align with the lateral axis 50 when the coupler 470 is assembled with the lower assembly 300, such as the mount 320. When assembled, the proximal end of the coupler 470 may rotate relative to the mount 320 and about the axis 50.

The body 471 may include a chassis attachment portion 475 at a distal end thereof. The chassis attachment portion 475 may be attached to or be integral with the portion 472. The portion 475 may extend away from an end of the portion 472 at an angle, as shown. The portion 475 may include an opening 476 extending therethrough. There may be a counter bore in the opening 476 as shown. The opening 476 may be aligned with and/or define a local axis 80A. The local axis 80A may align with the clutch axis 80 when the coupler 470 is assembled with the chassis 410. When assembled, the distal end of the coupler 470 may be rotationally fixed relative to the chassis 410 by a clutch, as further described.

The portion 462 at the distal end of the rocker 450 may be rotatably coupled with the chassis 410 by a coupler pivot shaft 495. (See FIG. 4B.) The shaft 495 may include a first end 495A and an opposite second end 495B. The shaft 495 may be an elongated structural element extending from the first end 495A to the second end 495B. The shaft 495 may be received through the openings 416, 420 of the chassis 410 to align with the chassis axis 70. The second end 495B may be received by the opening 420 of the second ear 418. The first end 495A may be received by the opening 416 of the first ear 414. The rocker receiving space 422 of the chassis 410 may receive the third ear 464 of the rocker 450, such that the shaft 495 extends through the opening 466 of the third ear 464. The shaft 495 may therefore rotatably couple the rocker 450 with the chassis 410 by securing the third ear 464 rotatably within the space 422 of the chassis 410.

In some embodiments, there may also be a bushing 496 and a bushing 497. The bushing 496 may be located with the first end 495A and the bushing 497 may be located with the second end 495B of the shaft 495. In some embodiments the mount attachment portion 454 of the rocker 450 may include one or more bushings. As shown, the first ear 456 and the second ear 458 may each receive a bushing 488 therein.

The distal end of the coupler 470 may be coupled with the chassis 410. As shown, the chassis attachment portion 475 of the coupler 470 may be coupled with the base 430 of the chassis 410. When assembled, the axis 80A defined by the coupler 470 may align with the axis 80B defined by the chassis 410. The axes 80A, 80B may align with the clutch axis 80 when assembled with the thumb 200. The distal end of the portion 475 that includes the opening 476 may be located with the opening 431 defined by the base 430 of the chassis 410.

The openings 476, 431 may receive therethrough a shaft 485A connected with a bevel gear 485, or portions thereof. The bevel gear 485 may have a series of bevel teeth on a first end with an elongated structural element extending therefrom, such as the shaft 485A. The shaft 485A of the bevel gear may extend through the opening 431 of the chassis 410 and the opening 476 of the coupler 470 to couple the components together. A nut 484 may rotatably attach to an end of the shaft 485A. In some embodiments, there may be a clutch assembly 479, as further described, which may be secured together by the nut 484. The clutch assembly 479 may prevent rotation of various parts about the clutch axis 80, as further described.

When the coupler 470 is assembled with the chassis 410, the distal end of portion 475 of the coupler 470 may be rotationally fixed about the clutch axis 80 relative to the chassis 410. The clutch assembly 479 may provide a compressive force that creates rotational resistance, as further described, at the connection between the coupler 470 and the chassis 410. In some embodiments, structures of the chassis 410 and/or coupler 470 may be positioned to prevent relative rotation therebetween. For example, a surface 433 of the chassis 410 may contact a surface 477 of the coupler 470 to prevent rotation. As further example, the ears 432 and/or 436 of the chassis 410 may prevent rotation of the distal end of the coupler 470. In some embodiments, the relative positioning and orientation of the axes 50A, 80A may prevent rotation of the coupler 470 about the clutch axis 80.

As shown in FIG. 4B, the thumb 200 may include the clutch assembly 479. The clutch assembly 479 may be located adjacent the chassis 410, for example in between the body 430 and the nut 484 attached to the bevel gear 485. As shown in FIG. 4B, the clutch assembly may include a friction plate bushing 480, a clutch brake plate 481, a friction plate 482, and/or one or more compression springs 483, shown here as Belleville washers. These components may be located in between the base 430 of the chassis 410 and the nut 484.

In some embodiments, the clutch assembly 479 may include the compression springs 483 to provide axially outward forces to create frictional rotational resistance of the bevel gear 485. For example, the compression spring 483 may be a Belleville washer or similar type structure. There may be multiple springs 483 stacked one on top of another. There may be one, two, three, four, five, six or more springs 483. The clutch assembly 479 may be designed such that the springs 483 and friction plate 482 prevent rotation of the bevel gear 485 when the thumb 200 is operated electronically, for example powered by an actuator. However, the friction may be overcome, and thus the bevel gear 485 rotated, manually. For example, the upper assembly 500 may be grasped by the user's other sound hand and rotated to overcome the friction in the clutch assembly 479. The nut 484 may be tightened accordingly to apply a desired compressive force on the spring 483 such that a desired frictional rotational resistance is provided to the bevel gear 485. The rotational resistance of the bevel gear 485 may prevent it from rotating about the clutch axis 80. Thus, when a corresponding bevel gear acts on the bevel gear 485, as further described herein, the bevel gear 485 and the structures to which it is fixedly attached, such as the coupler 370 and the chassis 410, may move to cause the rotation of the upper assembly 500 about the lateral axis 50.

The coupler 470 may further include a bushing 486. The bushing 486 may be located within the opening 473. The opening 473 may be in the mount attachment portion 472 that attaches rotatably to the lower assembly 300.

The coupler 470 at a proximal end thereof may be rotatably coupled with the lower assembly 300. The opening 473 of the mount attachment portion 472 of the coupler 470 may be rotatably coupled on the shaft 360 of the mount 320 of the lower assembly 300. The local axis 50A defined by the coupler 470 may align with the lateral axis 50 defined by the lower assembly 300 when assembled together. The proximal end of the coupler 470 may therefore rotate relative to the mount 320 about the lateral axis 50 on the shaft 360. The proximal end of the mount attachment portion 472 having the opening 473 may therefore be located between the second ear 326 and the second projection 330 of the mount 320.

The rocker 450 at a proximal end thereof may be rotatably coupled with the lower assembly 300. The mount attachment portion 454 of the rocker 450 may be rotatably coupled with the mount 320. The local axis 60A defined by the rocker 450 may be aligned with the rocker axis 60 of the mount 320 when assembled together. The openings 457, 459 of the rocker 450 may receive therethrough the shaft 350 of the lower assembly 300. Therefore, the rocker 450 may rotate about the rocker axis 60 on the shaft 350. When assembled together, the first and second ears 456, 458 of the rocker 450 may be located in between the first ear 324 and the second projection 330 of the mount 320.

The middle assembly 400 may include a sensing element 487. The sensing element 487 may be a magnet. The element 487 may be located within an opening 488 at the proximal end of the coupler 470. The opening 488 may be in the mount attachment portion 472 of the coupler 470. The opening 488 may receive the element 487 therein. In some embodiments, the element 487 is a magnet that interacts with the sensor 382 of the lower assembly 300, for example a Hall Effect sensor assembly. The element 487 and the sensor 382 may provide data related to the position of the coupler 470 relative to the mount 320. The data related to the relative position between the coupler 470 and the mount 320 may be used to control the thumb 200, as further described.

As further shown in FIGS. 4A and 4B, the middle assembly 400 may include a main shaft 489. The main shaft 489 may be an elongated structural element configured to rotatably couple the middle assembly 400 with the upper assembly 500, as further described. The shaft 489 may be received through and/or secured within the openings 434, 438 of the swaying chassis 410. The main shaft 489 may include a first end 489A and a second end 489B. The second end 489B may be received in and/or through the opening 434 and the first end 489A may be received in and/or through the opening 438 of the chassis 410. The shaft 489 may extend between the first ear 432 and the second ear 436 of the chassis 410. In some embodiments, the openings 434, 438 may include a bushing 498 located therein.

The shaft 489 may have located thereon various components. As shown, the shaft may include a worm wheel 490, a bushing 491, a bevel gear 492 and a worm wheel 493. The worm wheel 490 may be located near the first ear 432 and the worm wheel 493 may be located near the second ear 436. The worm wheels 490, 493 may be spaced apart from each other. In between the worm wheels 490, 493 may be located the bevel gear 492. In some embodiments, the bushing 491 is located between the worm wheel 490 and the bevel gear 492.

The worm wheels 490, 493 may be in mechanical communication with corresponding worm gears 534, 542 as further described. The worm wheel 490 is rotationally fixed on the shaft 489 about the axis 90. The worm wheel 490 may be rotationally fixed by a pin 494. The pin 494 may extend into or through the wheel 490, and into or through the first ear 432 of the chassis 410, to prevent the wheel 490 from rotating about axis 90. The pin 494 may extend into or through the opening 435 (shown in FIG. 4C) of the chassis 410. The rotationally-fixed worm wheel 490 may interact with the worm gear 534 to cause a pinch rotation about the axis 90, as further described.

The worm wheel 493 is rotatably coupled on the shaft 489 about the axis 90. The bevel gear 492 is also rotatably coupled on the shaft 489 about the axis 90. The bevel gear 492 is rotationally fixed with the worm wheel 493. Rotation of the worm wheel 493 about the axis 90 will thus cause a corresponding rotation of the bevel gear 492 about the axis 90. The bevel gear 492 may mechanically communicate with the bevel gear 485. The mechanical communication between the bevel gears 485, 492 may cause the upper assembly 500 to rotate about the lateral axis 50, as further described.

Figure 4F:
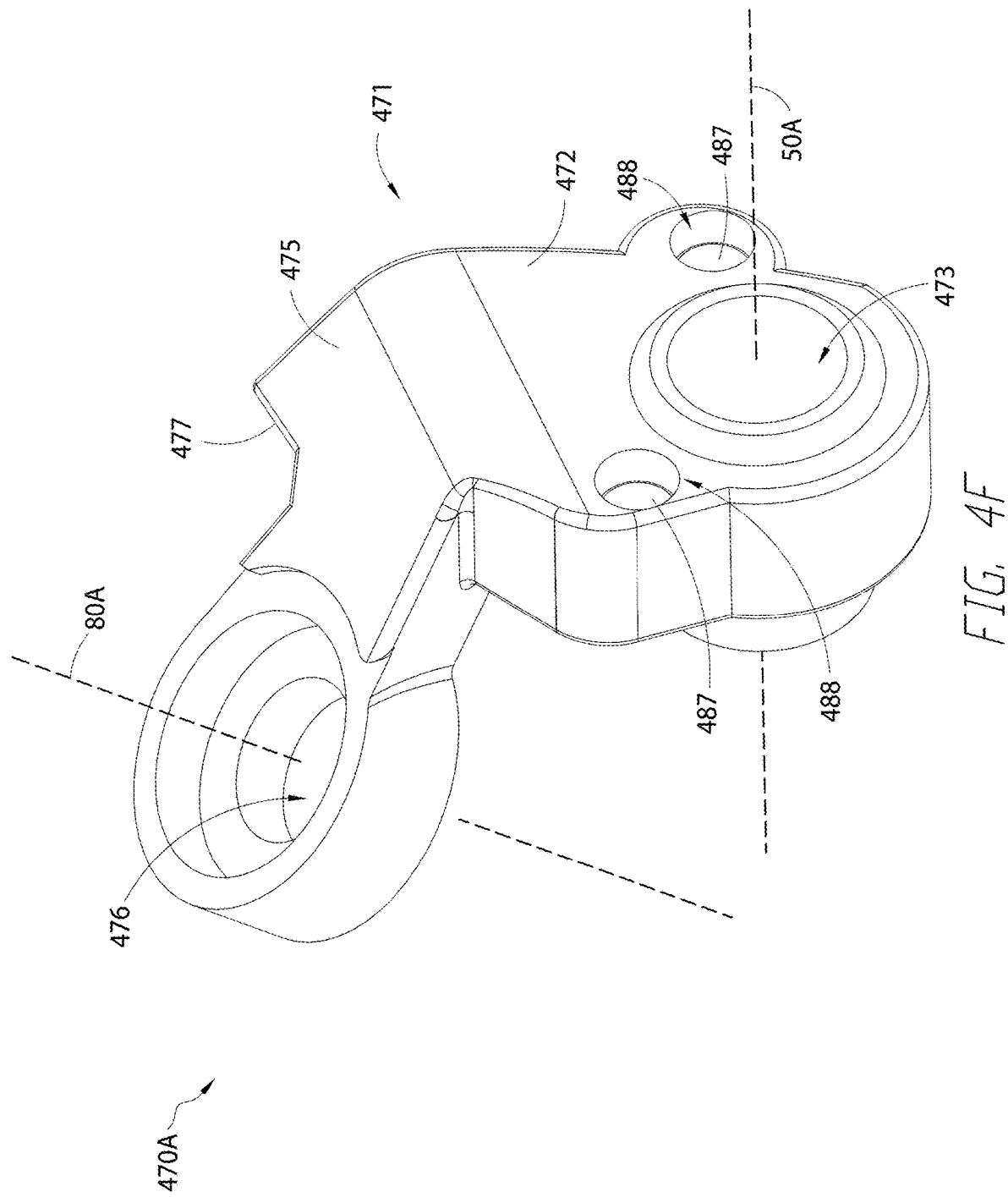
FIG. 4F is a perspective view of another embodiment of a coupler that may be used with the thumb of FIGS. 1A and 1B.

FIG. 4F is a perspective view of another embodiment of a coupler 470A that may be used with the thumb 200. The coupler 470A may have the same or similar features and/or functions as the coupler 470 described herein. In addition or alternatively to features described with respect to the coupler 470, the coupler 470A in some embodiments may include, for example, more than one sensing element 487. The sensing elements 487 may be magnets. The coupler 470A may include a first sensing element 487 such as a first magnet with a first polarity and a second sensing element 487 such as a second magnet with a second polarity opposite the first polarity. The elements 487 may be disposed in openings 488 on opposite sides of the coupler 470A. The openings 488 may be in the mount attachment portion 472 of the coupler 470A. The mount attachment portion 472 may protrude or extend (e.g., include additional surface area) to accommodate additional openings 488 and/or elements 487.

The middle assembly 400 may include two sensing elements 487 which allow for the reduction of external noise during the calculation of the position of the coupler 470A relative to the mount 320. One of the sensing elements 487 may be disposed close to the sensor 382 when the thumb 200 is rotated away from a palm of a hand. This can allow the element 487 to be close enough to the sensor 382 when the thumb 200 is rotated away from the palm, towards a lateral position, to overcome background and/or outside noise, e.g., from electro-magnetic compatibility (EMC) influence, such as electrostatic discharge (ESD), electromagnetic interference (EMI), or radio frequency interference (RFI), or from the earth's magnetic field, that might otherwise interfere with the sensor's 382 functionality. This can improve the accuracy of the estimated rotation of the thumb 200.

In some embodiments, when the thumb 200 is rotated towards the palm there is a strong positive magnetic signal, and when the thumb 200 is rotated away from the palm there is a strong negative magnetic signal. The presence of a strong magnetic signal when the thumb 200 is in each of the aforementioned positions can reduce the effect of external noise on the sensor 382 and thereby increase the accuracy of calculations of the thumb's 200 rotation.

One or more of the sensors 382 and/or elements 487 may be disposed about various axes. The sensors 382 and/or elements 487 may be disposed about the local axis 50A of the coupler 470A and/or the rocker axis 60 of the rocker 450, for example within the second projection 330 of the mount 320. Sensors 382 and/or elements 487, such as magnets, which are disposed about the local axis 50A may provide information about the rotational position of the thumb 200. Sensors 382 and elements 487, such as magnets, which are disposed about, for example, the local axis 50A can provide information about the position of the thumb 200 about the local axis 50A. Sensors 382 and elements 487 can be disposed about both the local axis 50A and/or the rocker axis 60 to provide information about the absolute position of the thumb 200 along both axes. In addition or alternatively, in some embodiments, the sensors 382 and/or elements 487 may be disposed about the local axis 80A of the coupler 470A.

Figure 5B:
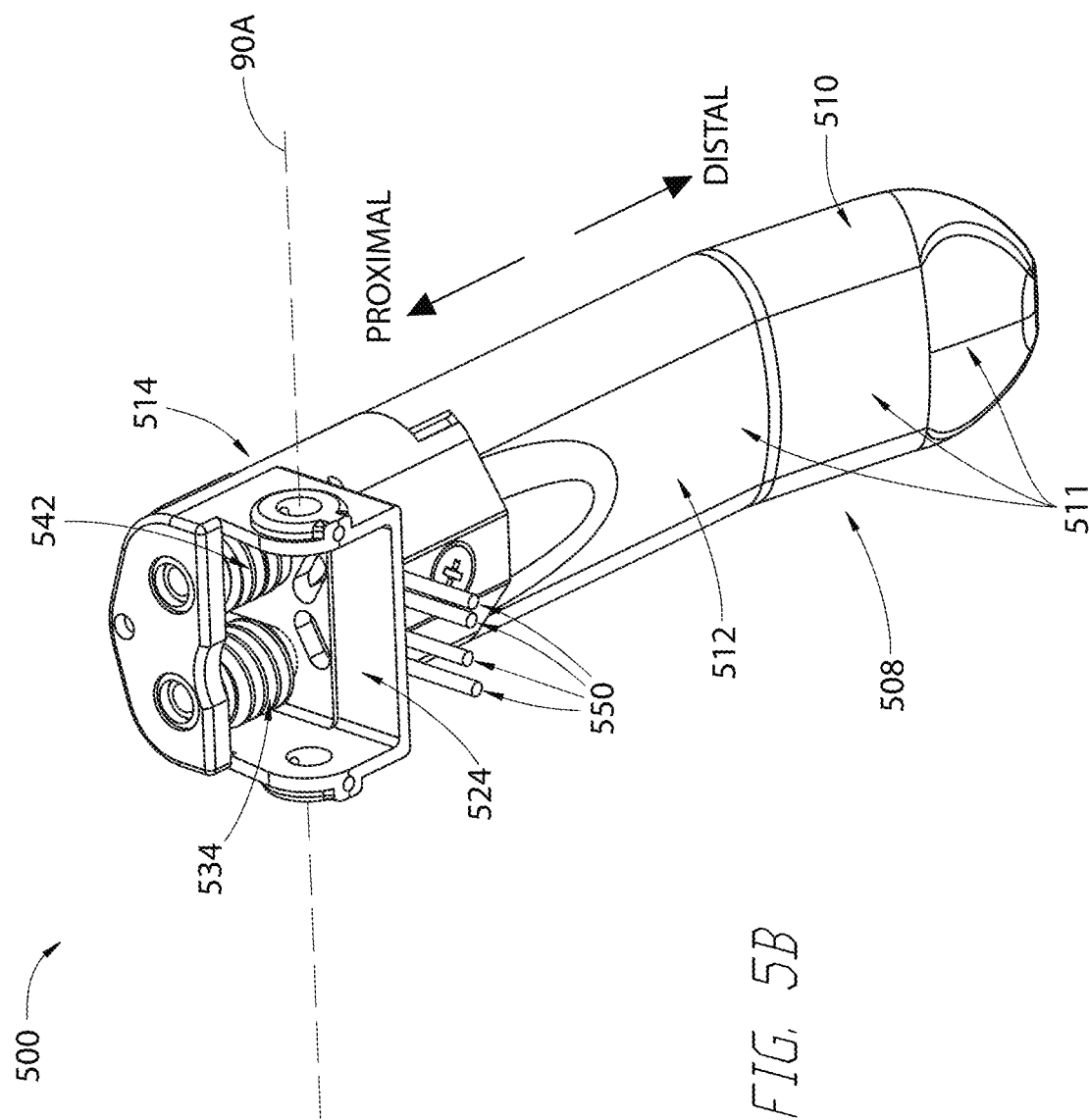
Figure 5C:
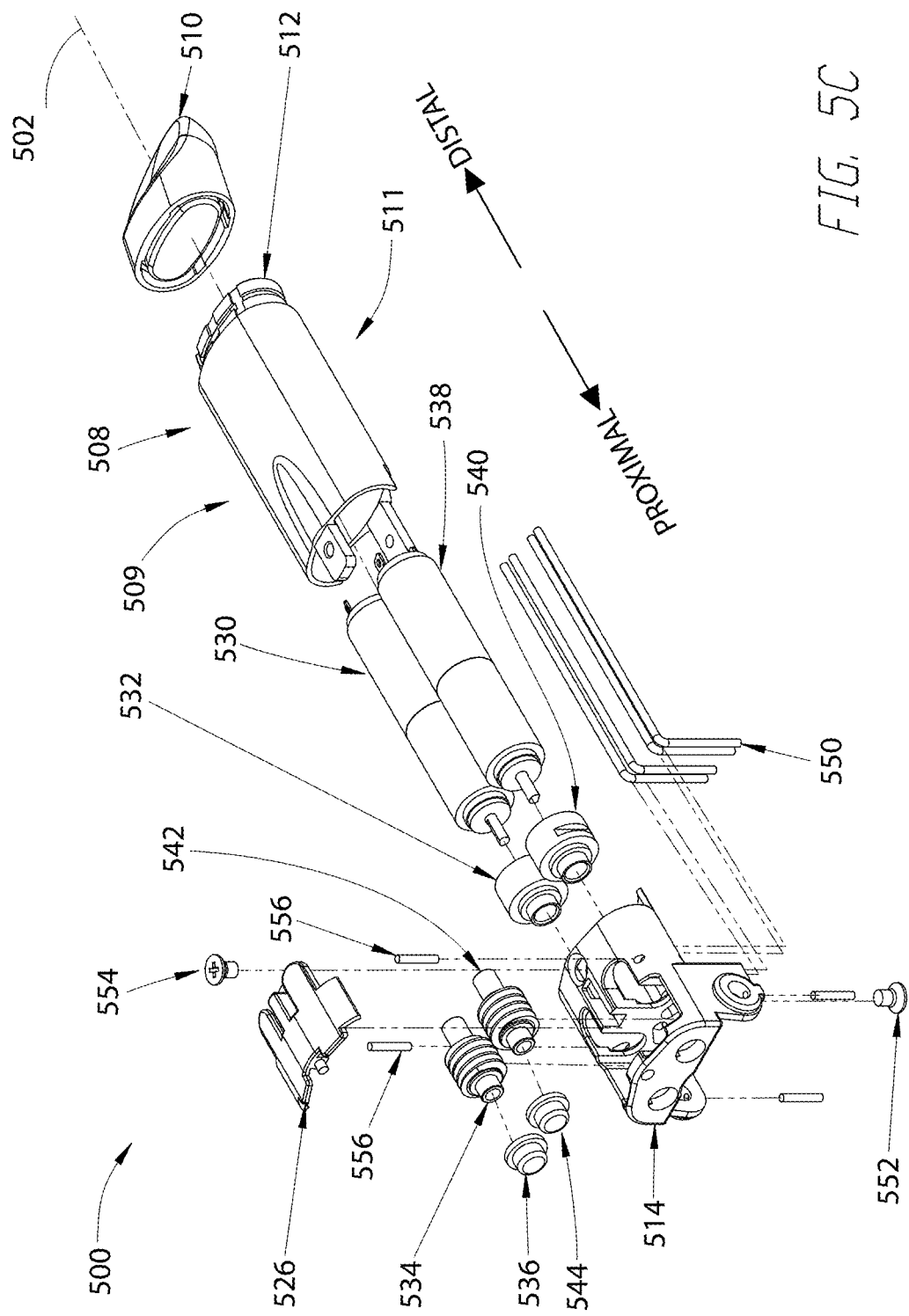
FIG. 5C is an exploded view of the upper assembly of FIGS. 2A-2C.

FIGS. 5A and 5B are perspective views of the upper assembly 500. FIG. 5C is an exploded view of the upper assembly 500. The upper assembly 500 may be described with respect to distal and proximal directions, as indicated in FIGS. 5A-5C. The upper assembly 500 may include a cover 508. As shown in FIG. 5C, the upper assembly 500 or portions thereof may extend along and define a thumb longitudinal axis 502. The cover 508 may extend along the axis 502. As mentioned, the upper assembly 500 may be or include the digit, such as the thumb digit, that is rotated about the axes 50 and/or 90. For example, the cover 508 may provide the outer structure for the digit that is rotated.

The cover 508 may provide a cover or housing for various components of the upper assembly 500. The cover 508 may be a single piece or multiple pieces. As shown, the cover 508 may include a distal tip cover 510, a lower cover 512, and a actuator housing 514. The distal cover 510 may cover a distal end of the upper assembly 500. The distal tip may be fully rubber or other materials that provide high friction, better grip at all positions, and is flexible to allow large forces for gripping/pinching.

The lower cover 512 may be attached to the distal cover 510. The actuator housing 514 may be attached to the lower cover 512. The various components of the cover 508 may have a thumb shape or a general thumb shape.

The cover 508 may include a gearing cover 526. As shown, the cover 526 may be part of the housing 514. The housing 514 may include an opening 515 and an opening 517 on a proximal end thereof. The opening 515 may include a bushing 536 therein. The opening 517 may include a bushing 537 therein. The openings 515, 517 may support ends of corresponding bushings 536, 544, as further described.

The cover 508 may include a first ear 516 and a second ear 520. The first and second ears 516, 520 may be located at a proximal end of the cover 508. The first and second ears 516, 520 may extend away from the cover 508 to define therebetween a main shaft receiving space 524. The space 524 may receive therein the main shaft 489 and the various components thereon, as described in further detail for example with respect to FIG. 4B. The first ear 516 may include an opening 518 extending therethrough. The second ear 520 may include an opening 522 extending therethrough. The main shaft 489 may be supported by the first and second ears 516, 520. The first end 489A of the shaft 489 may be supported within the opening 522 of the second ear 520. The second end 489B of the shaft 489 may be supported by the opening 518 of the first ear 516.

The openings 518, 522 may be aligned with each other and define a local axis 90A. The axis 90A may align with the main shaft 489 when the shaft 489 is located within the receiving space 524. The axis 90a may align with the pinch axis 90 when assembled with the middle assembly 400. The upper assembly 500 may rotate about the pinch axis 90.

As shown in FIG. 5B, the upper assembly 500 may include one or more actuator wires 550. As shown, the actuator wires 550 may extend away from a proximal end of the upper assembly 500. The actuator wires 550 may be connected to a processor, for example via the actuator cable circuit board 378.

As shown in FIG. 5B, the upper assembly 500 may include a first worm gear 534. The upper assembly 500 may include a second worm gear 542. The worm gears 534, 542 may be rotated by one or more actuators 530, 538, as further described. The worm gears 534, 542 may be located adjacent the receiving space 524. The gears 534, 542 may mechanically communicate respectively with the worm wheels 490, 493 of the middle assembly 400. Mechanical communication of the worm gears 534, 542 with the worm wheels 490, 493 may cause the upper assembly 500 to rotate about the pinch axis 90 and/or the lateral axis 50, as further described.

The upper assembly may include a first actuator 530. The upper assembly 500 may include a second actuator 538. In some embodiments, the upper assembly 500 may include only one of the actuators. In some embodiments, the upper assembly 500 may include more than two actuators. As shown, the first actuator 530 may be in mechanical communication with the first worm gear 534. The first actuator 530 may actuate, for example rotate, the first worm gear 534. In some embodiments, the upper assembly 500 may include a first actuator bushing 532. The actuator bushing 532 may be attached to a proximal end of the first actuator 530 and/or a distal end of the first worm gear 534. A proximal end of the first worm gear 534 may be coupled with a bushing 536 which may be secured with the opening 515 of the cover 508.

The upper assembly may include the second actuator 538. The second actuator 538 may be in mechanical communication with a second worm gear 542. The second actuator 538 may actuate, for example rotate, the second worm gear 542. In some embodiments, the second actuator 538 may be coupled with a second actuator bushing 540. The second actuator bushing 540 may be located at a proximal end of the second actuator 538. A proximal end of the second worm gear 542 may be coupled with a bushing 544. The bushing 544 may be may be secured with the opening 517 of the cover 508.

The first and/or second actuator 530, 538 may extend along or parallel to the longitudinal axis 502. As shown, the actuators 530, 538 are located adjacent to each other within the cover 508 and extend along the longitudinal axis 502. The first and second worm gears 534, 542 are located at a proximal end of the upper assembly 500. The actuators 530, 538 actuate the respective worm gears 534, 542 to cause rotation of the upper assembly 500 about the axis pinch 90, as further described.

The upper assembly 500 may include the gearing cover 526 located above the first and second worm gears 534, 542. In some embodiments, the upper assembly 500 may include one or more pins 556. In some embodiments, the upper assembly 500 may include a screw 552 and a screw 554. The screws 552, 554 may attach to various components of the upper assembly 500. In some embodiments, other suitable attachments besides fasteners may be used, for example adhesives, ties, or other suitable means.

The upper assembly 500 may rotate about a first axis and/or a second axis. The upper assembly 500 may rotate simultaneously about the first axis and the second axis. The upper assembly 500 may rotate about only the first axis or only about the second axis.

In some embodiments, rotation of the upper assembly 500 about the first and second axes may mimic rotation of a human sound thumb by performing rotations about axes where the axes are moving relative to a fixed reference frame, such as the mount 320. The first axis may be the pinch axis 90, for example as shown in FIGS. 2A to 2C. The second axis may be the lateral axis 50, for example as shown in FIGS. 2B and 2C. The upper assembly 500 may rotate simultaneously about the axes 50, 90 to mimic movement of a sound thumb. Rotation of the upper assembly 500 about the lateral axis 50 may result in a sweeping motion of the upper assembly 500 about the lateral axis 50. This sweeping motion of the upper assembly 500 may resemble an arc. The sweeping motion may cause the upper assembly 500 to effectively rotate about a local longitudinal axis extending along the digit due to the separation of the lateral axis 50 from the rotating digit.

The upper assembly 500 may rotate about the various axes by actuating the first actuator 530 and/or the second actuator 538. Rotation of the first worm gear 534 by the first actuator 530 may cause the upper assembly 500 to rotate about the pinch axis 90. Rotation of the second worm gear 542 by actuation of the second actuator 538 may, depending on the speed of rotation, allow for rotation about only the pinch axis 90 or cause rotation of the upper assembly 500 about the lateral axis 50. In some embodiments, only one of the actuators 530, 538 may be actuated at a time. In some embodiments, both of the actuators 530, 538 may be actuated at a time. In some embodiments, the first and second actuators 530, 538 may be actuated simultaneously. Actuation of the first actuator 530 may contribute to rotation of the upper assembly 500 about the pinch axis, while actuation of the second actuator 538 may contribute to rotation of the upper assembly 500 about both the pinch axis 90 and the lateral axis 50.

Rotation of the upper assembly 500 about the pinch axis 90 may be due to mechanical communication between the rotating worm gear 534 and the worm wheel 490. That is, rotation of the first worm gear 534 may cause interaction with the worm wheel 490. Interaction of the gear teeth of the first worm gear 534 with the complementary projections of the worm wheel 490 will cause the gear 534 to advance along the outer circumference of the wheel 490. Advancement of the gear 534 along the wheel 490 will cause the upper assembly 500 to rotate in an open or closed direction about the pinch axis 90, depending on the direction of rotation of the worm gear 534. By "open" it is meant that the upper assembly 500 moves in a direction associated with opening a grip. For example, the upper assembly 500 may open by rotating away from a palm of the hand 120. By "closed" it is meant that the upper assembly 500 moves in a direction associated with closing a grip. For example, the upper assembly 500 may close by rotating away toward a palm of the hand 120.

Further, the pinch axis 90 may change orientation relative to a fixed reference frame, such as the mount 320, which may be fixed to the hand 120 or other component and may be considered an example of a fixed reference frame for purposes of description of the moving axes. The pinch axis 90 may change orientation due to lateral rotation of the upper assembly 500 about the lateral axis 50. The pinch axis 90 may rotate about the lateral axis 50 during lateral rotation. The pinch axis 90 may make a sweeping motion while rotating, as described with respect to lateral rotation of the digit, for example due to separation between the pinch axis 90 and the lateral axis 50. Thus, when the upper assembly 500 is later rotated about the pinch axis 90 after rotating about lateral axis 50, the orientation of the pinch axis 90 relative to the mount 320 may have changed. For example, the pinch axis 90 may move relative to the mount 320 as the upper assembly 500 rotates. The pinch axis 90 may move to change angles and/or planes.

As the upper assembly 500 rotates about the pinch axis 90, the second worm gear 542 will also rotate with the upper assembly 500 about the axis 90. The second worm gear 542 may have a series of teeth that interact with a series of projections on the worm wheel 493. Because the worm wheel 493 is rotationally fixed with the bevel gear 492, the bevel gear 492 will also rotate about the pinch axis 90 and thereby act against the bevel gear 485, which causes lateral rotation, as further described. Therefore, appropriate rotation of the bevel gear 492 during pinch axis rotation will allow for rotation of the upper assembly 500 about the pinch axis. For example, the bevel gear 492 may be rotated by the second actuator 538 at a particular speed and direction in order to allow for the first actuator 530 to cause the desired pinch rotation. The bevel gear 492 may be rotated at a corresponding speed and direction to move the teeth of gear 492 between the teeth of gear 485 in order to not transmit forces to the gear 485 sufficient to induce lateral rotation of the upper assembly 500 about the lateral axis 50. In this way, the upper assembly 500 may rotate only about the pinch axis 90. The corresponding speed of rotation of the bevel gear 492 to only allow for pinch axis rotation will depend on the particular geometry of the bevel gear 492 and bevel gear 493, such that the teeth of each gear 492, 493 will not interact in a manner to cause lateral rotation. If lateral rotation about the lateral axis 50 while rotating about the pinch axis 90 is desired, the bevel gear 492 may be rotated at a different speed, as further described.

Rotation of the upper assembly 500 about the lateral axis 50 may be due to mechanical communication between the rotating worm gear 542 and the worm wheel 493, which rotates the bevel gear 492, as described. Further, the clutch axis 80 may align with the axes 80A and 80B as shown respectively in FIGS. 4E and 4C. The clutch axis 80 may further align with the shaft 485A of the bevel gear 485. As described, a shaft 485A of the bevel gear 485 may extend through the opening 476 of the coupler 470 and the opening 431 of the swaying chassis 410 and secure together the coupler 470 and chassis 410 with the nut 484 and clutch assembly 479. The bevel gear 485 may thus be rotationally connected about the clutch axis 80 due to the clutch assembly 479 with a certain amount of rotational resistance.

The mechanical communication of the bevel gear 492 with the bevel gear 485 may cause relative rotation between the swaying chassis 410 and the mount 320. This relative rotation may be about the lateral axis 50. The bevel gear 485 may be rotationally fixed due to the clutch assembly 479 such that the interaction of teeth of the bevel gear 492 with teeth of the bevel gear 485 will apply a lateral force to the bevel gear 485 and thus the distal end of the coupler 470 and chassis 410, to cause the chassis 410 to move, for example sway. This lateral movement of the chassis 410 will cause movement of the coupler 470 and rocker 450. The proximal end of the coupler 470 will rotate about the axis 50 relative to the mount 320, the proximal end of the rocker 450 will rotate about the axis 60 relative to the mount 320, and the distal end of the rocker 450 will rotate about the axis 70 relative to the chassis 410. This movement will cause the upper assembly 500, which is coupled with the chassis 410, to rotate about the lateral axis 50 relative to the mount 320. Thus, the upper assembly 500 may perform a sweeping motion, as described, as the upper assembly 500 moves due to separation of the upper assembly 500 and the lateral axis 50.

Further, as the chassis 410 rotates, the orientation of the clutch axis 80 may change as well, for example with respect to the mount 320. For example, the clutch axis 80 may move relative to the mount 320 as the upper assembly 500 rotates. The clutch axis 80 may move to change angles and/or planes. Because the chassis 410 will be moving relative to the mount 320, the clutch axis 80 will also be moving relative to the mount 320.

Simultaneous rotation of the upper assembly 500 about the pinch axis 90 and lateral axis 50 may be due to mechanical communication between the rotating worm gears 534, 542 and the respective worm wheels 490, 493. The interactions may be as described above individually for pinch and lateral rotation, but with the worm gear 542 rotating the worm wheel 493 (and thus bevel gear 492) at an appropriate speed. For example, the bevel gear 492 may be rotated at a sufficiently slow or fast speed to cause the lateral forces described above to be imparted on the bevel gear 485 to cause the movement of the chassis 410 and the rotation about the lateral axis 50. The desired direction of lateral rotation can be controlled by the direction of rotation of the bevel gear 492.

Figure 6:
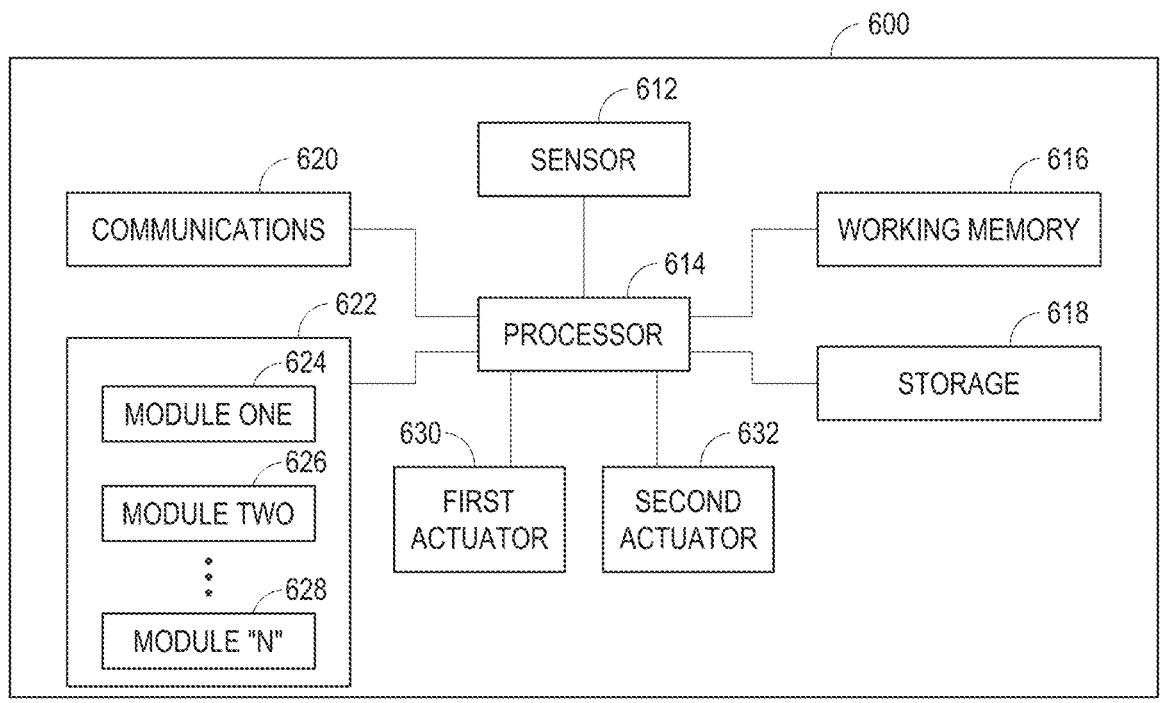
FIG. 6 is a block diagram of an embodiment of a powered prosthetic thumb.

The various devices and systems discussed herein may be embodied in software and/or hardware in a number of configurations. FIG. 6 is a block diagram of an embodiment of a thumb 600. The thumb 600 may have the same or similar features and/or functionalities as the thumb 200, and vice versa. In some embodiments, some or all of the components of the thumb 600 are shared with the hand 120.

The thumb 600 has a set of components including a processor 614 in electrical communication with a sensor 612, a working memory 616, a memory storage 618, first and second actuators 630, 632, a communications subsystem 620, and a module memory 622. The components may be in communication via wired or wireless connections.

In some embodiments, the sensor 612 may be the sensor 382, such as a Hall Effect sensor. The first actuator 630 may be the actuator 530. The second actuator 632 may be the actuator 538. The processor 614 may be part of the board 374 or 378. The processor 614 may be separate from the thumb 600 and be located on the hand 120. The processor 614 may be a general purpose processing unit or a processor specially designed for prosthetic applications. A general purpose processor can be a microprocessor, but in the alternative, the processor can be any conventional processor, controller, microcontroller, or state machine. The working memory 616 may be used by the processor 614 to store a working set of processor instructions contained in the modules of memory 622. Alternatively, working memory 616 may also be used by the processor 614 to store dynamic data created during the operation of the thumb 600.

In some embodiments, the processor 614 is configured by the several modules stored in the memory 622. The modules in memory 622 may be software, such as programs or applications. A plurality of modules may be in the thumb 600. These modules include instructions that configure the processor 614 to perform various control or other type tasks. In the embodiment shown, the memory 622 stores module one 624, module two 626, etc. to module "N" 628. The modules may be related to, for example, processing data from the sensor 612, detection of current orientation of the thumb 600, determination of how to achieve a desired orientation with the thumb 600, commanding the thumb 600 for example the actuators 630, 632 to perform a rotation or movement, tracking movement of the thumb 600, etc. Further example methods of operation of the modules are further described herein, for example with respect to FIG. 7.

The memory 622 may include an operating system module, such as module one 624, that configures the processor 614 to manage the memory and processing resources of the thumb 600. For example, the operating system module may include device drivers to manage hardware resources such as the sensor 612, actuators 630, 632, or storage 618. Instructions contained in the modules of memory 622 may thus not interact with these hardware resources directly, but instead interact through standard subroutines or APIs located in an operating system component. Instructions within the operating system may then interact directly with these hardware components.

In some embodiments, the operating system and/or other modules or components of the thumb 600 are on a separate device, such as a mobile device or remote processor. For example, the operating system may be a remote operating system of a remote device that is in communication with the thumb 600 via the communications subsystem 620. The mobile operating system may be on a mobile device, such as a smartphone, and may be Google's Android, Apple's iOS, Symbian, Blackberry Ltd's BlackBerry 10, Samsung's Bada, Microsoft's Windows Phone, Hewlett-Packard's webOS, embedded Linux distributions such as Maemo and MeeGo, Mozilla's Firefox OS, Canonical Ltd.'s Ubuntu Phone, Tizen, or others. The remote device can receive multiple operating system module updates over its lifetime.

The processor 614 may write data to the storage 618. While the storage 618 may be a traditional disk device, it may also be a disk based storage device or one of several other type storage mediums to include a memory disk, USB drive, flash drive, remotely connected storage medium, virtual disk driver, or the like.

FIG. 6 depicts the thumb 600 comprising separate components to include a processor, imaging sensor, and memory, however these separate components may be combined in a variety of ways to achieve particular design objectives. For example, in an alternative embodiment, the memory components may be combined with processor components to save cost and improve performance. Further the memory components may be combined with each other.

Figure 7:
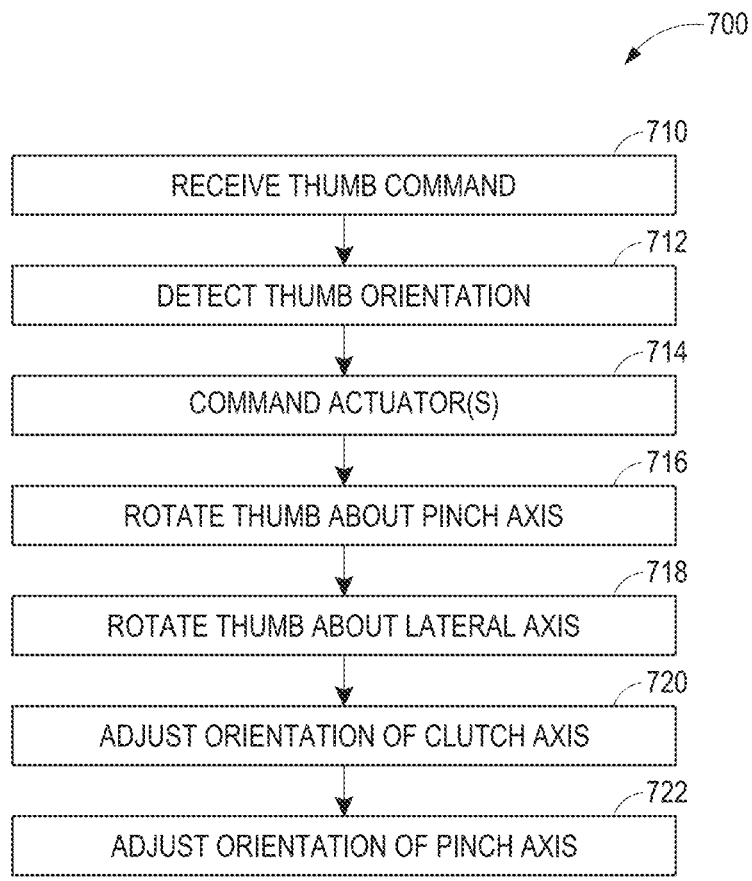
FIG. 7 is a flow chart showing an embodiment of a method of rotating a powered prosthetic thumb.

FIG. 7 is a flow chart showing an embodiment of a method 700 of rotating a powered prosthetic thumb. The method 700 may be performed by the thumb 200 or 600. Other rotations and movements may also be performed besides those described in the method 700. For example, the thumb may include other joints along the digit that rotate as well.

The method 700 begins with block 710 wherein a thumb command is received. The thumb command may be a command to perform a particular rotation or form a desired orientation or grip. The command may include instructions to perform a pinch rotation of the upper assembly 500 about the pinch axis 90 and/or a lateral rotation about the lateral axis 50. Block 710 may include the thumb 200 receiving a command via the board 374, or the thumb 600 may receive a command via the communications subsystem 620. The command may be manually communicated from a user or automatically generated in response to detecting certain preconditions that trigger automatic movement. The command may be generated via gesture control or other techniques, for example techniques as described in U.S. Pat. No. 8,696,763, titled PROSTHETIC APPARATUS AND CONTROL METHOD and issued on Apr. 15, 2014. The processor 614 may receive the command and query one or more modules of memory 622 and/or memories 616, 618.

The method 700 next moves to block 712 wherein the thumb orientation is determined. The orientation of the thumb 200 or 600 or portions thereof may be determined. The orientation may be determined using the sensors 382 and element 487, such as a Hall Effect sensor and a magnet as described. The sensor 612 may be used. Data from the sensors may be communicated and/or processed by the processor 614 or the board 374, 387. The data may be analyzed by running one or more of the modules in memory 622 or with memories 616, 618. The orientation may be used to determine which movements of the upper assembly 500 are needed to achieve the desired orientation as commanded in block 710.

The method 700 next moves to step 714 wherein the actuators are commanded to effect the movement of the thumb 200 or 600. The actuators 630 and/or 632 may be commanded. The actuators 530 and/or 538 may be commanded. The actuators may be commanded to perform a rotation of the upper assembly 500 about the pinch axis 90 and/or lateral axis 50. The actuators may be commanded to actuate, for example rotate, as various speeds or according to various operating profiles, such as ramp up, constant, ramp down. The actuators may be operated at desired speeds and directions to cause a desired lateral or pinch rotation, as described above.

The method 700 next moves to block 716 wherein the upper assembly 500 rotates about a pinch axis. The pinch axis may be the pinch axis 90. The actuator 530 or 630 may be commanded, for example to rotate in a first direction. The actuators may actuate in the manners described herein. The rotation may be mechanically communicated as described herein, for example with mechanical communication between the actuator 530, worm gear 534, and worm wheel 490.

The method 700 next moves to block 718 wherein the upper assembly 500 rotates about a lateral axis. The lateral axis may be the lateral axis 50. The actuator 538 or 632 may be commanded, for example to rotate in a first direction. The actuators may actuate in the manners described herein. The rotation may be mechanically communicated as described herein, for example with mechanical communication between the actuator 538, worm gear 542, worm wheel 493, and bevel gears 492 and 485. The rotation shown and described with respect to FIGS. 2D-2E may be effected. In some embodiments, block 718 may not be performed, for example where rotation is only about the pinch axis. In some embodiments, blocks 716 and 718 are performed simultaneously, for example where the digit rotates about both axes 50, 90 simultaneously.

The method 700 next moves to block 720 wherein the orientation of a clutch axis is adjusted. The clutch axis 80 may be adjusted. The clutch axis 80 may be adjusted due to rotation of the thumb 200 or 600, for example the upper assembly 500, about the lateral axis 50, which may move the clutch axis, as described. The orientation of the clutch axis may be adjusted relative to a fixed reference frame, such as the mount 320. In some embodiments, block 720 may not be performed, for example where rotation is only about the pinch axis and the clutch axis does not change orientation.

The method 700 next moves to block 722 wherein the orientation of a pinch axis is adjusted. The pinch axis 90 may be adjusted. The pinch axis may be adjusted due to rotation of the thumb 200 or 600, for example the upper assembly 500, about the lateral axis 50, which may move the pinch axis, as described. The orientation of the pinch axis may be adjusted relative to a fixed reference frame, such as the mount 320. In some embodiments, blocks 720 and 722 are performed simultaneously, for example where the thumb rotates about both axes 50, 90 simultaneously.

In some embodiments, two or more of the steps of the method 700 may be performed simultaneously. For example, all steps of the method 700 may be performing at the same time. Steps 714, 716, 718, 720 and 720 may all be performing at the same time. Other combinations of multiple steps may be performed simultaneously, as will be apparent from the description herein.

Figure 8A:
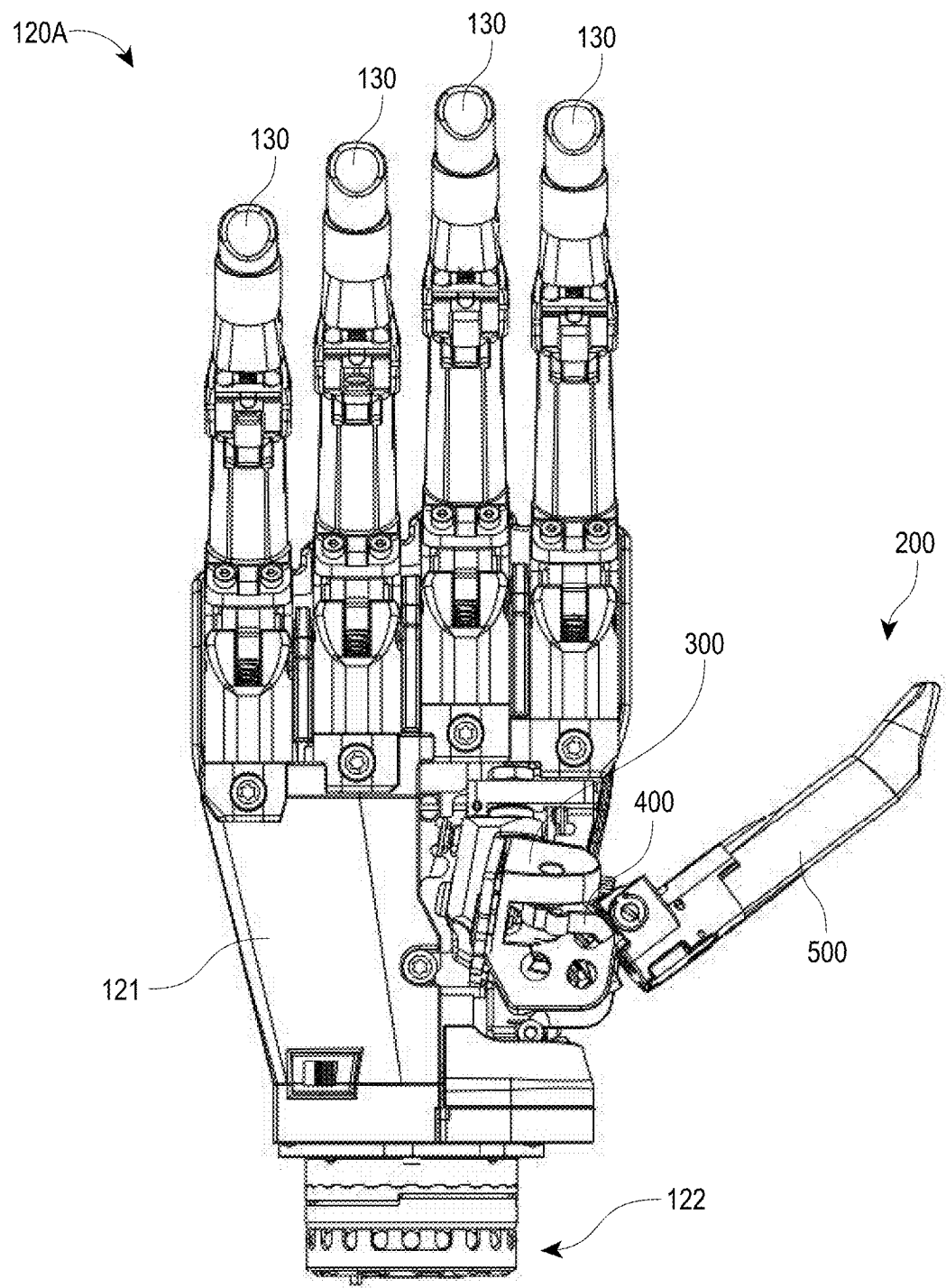
FIGS. 8A and 8B are front and back views respectively of an embodiment of a partial prosthetic hand having the thumb of FIGS. 1A and 1B attached to the partial prosthetic hand.
Figure 8B:
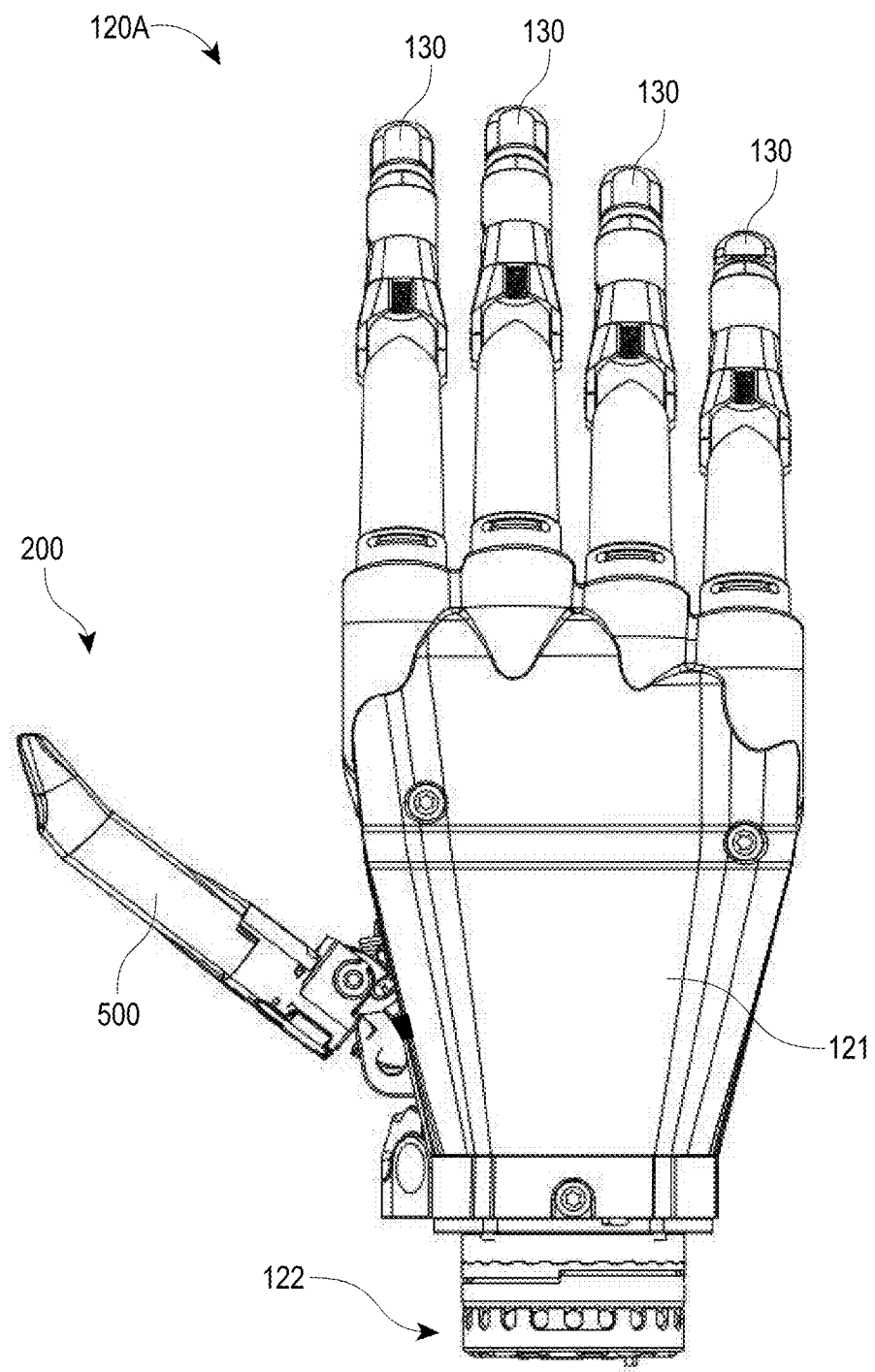

FIGS. 8A and 8B are front and back views respectively of an embodiment of a partial prosthetic hand 120A having the thumb 200. The hand 120A may have only four finger digits 130 attached to a palm 121. The hand 120A may have a wrist connector 122 configured to attach the hand to an arm, such as a prosthetic arm, or to a corresponding connector on a prosthetic or natural arm. The hand 120A may be configured to have a thumb attached to it. The thumb 200 may be attached to the hand 120A as shown. The lower assembly 300 of the thumb 200 may attach to the hand 120A, such as to the palm 121. The thumb 200 may be operated on the hand 120A in conjunction with the other digits 130 to form desired grips or other movements. The thumb 200 may be attached to a variety of different hands, such as a hand that is partially prosthetic and partially natural. The thumb 200 may attach directly to a residual (natural) or prosthetic arm or palm, such as the arm 110 or palm 124 as shown and described with respect to FIGS. 1A and 1B.

Various modifications to the implementations described in this disclosure can be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Any specific order or hierarchy of steps or blocks in any disclosed process is an example of a sample approach. Based upon design preferences, it is understood that the specific order or hierarchy of steps or blocks in the processes can be rearranged while remaining within the scope of the present disclosure. Any accompanying that claims present elements of the various steps or blocks in a sample order are not meant to be limited to the specific order or hierarchy presented.

A person/one having ordinary skill in the art would appreciate that any of the various illustrative logical blocks, modules, controllers, means, circuits, and algorithm steps or blocks described in connection with the aspects disclosed herein can be implemented as electronic hardware (e.g., a digital implementation, an analog implementation, or a combination of the two, which can be designed using source coding or some other technique), various forms of program or design code incorporating instructions (which can be referred to herein, for convenience, as "software" or a "software module"), or combinations of both.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. In some cases, the actions recited in the claims can be performed in a different order and still achieve desirable results.

In general, terms used herein are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A powered prosthetic thumb, comprising:
   a mount;
   a digit rotatably coupled with the mount about a first axis and a second axis, the first axis non-parallel with the second axis;
   an actuator configured to cause rotation of the digit about the first axis;
   a second actuator configured to cause the digit to rotate about the second axis; and
   a first bevel gear and a second bevel gear in mechanical communication with the first bevel gear;
   wherein an orientation of the first axis relative to the mount changes as the digit rotates about the second axis;
   wherein the second actuator is configured to cause rotation of the digit about the second axis by causing rotation of the first bevel gear.

2. The powered prosthetic thumb of claim 1, wherein the actuator is configured to rotate in a first direction to cause the digit to rotate about the first axis.

3. The powered prosthetic thumb of claim 1, wherein an orientation of the first axis relative to the second axis changes as the digit rotates about the second axis.

4. The powered prosthetic thumb of claim 1, wherein the first axis rotates about the second axis as the digit rotates about the second axis.

5. The powered prosthetic thumb of claim 1, further comprising a clutch assembly configured to allow for manual rotation of the digit about the second axis.

6. The powered prosthetic thumb of claim 1, further comprising a first worm wheel and a first worm gear in mechanical communication with the first worm wheel, wherein the actuator is configured to cause rotation of the digit about the first axis by causing rotation of the first worm gear.

7. The powered prosthetic thumb of claim 1, further comprising a chassis rotatably coupling the mount with the digit.

8. The powered prosthetic thumb of claim 7, further comprising a first link and a second link, each link rotatably coupling the chassis with the mount.

9. The powered prosthetic thumb of claim 1, wherein the first axis is a pinch axis, such that rotation of the digit about the first axis causes the digit to open or close, and the second axis is a lateral axis, such that rotation of the digit about the second axis causes lateral rotation of the digit.

10. The powered prosthetic thumb of claim 1, wherein the digit comprises the first actuator.

11. The powered prosthetic thumb of claim 1, wherein the mount is configured to couple with a prosthetic socket mounted on a residual limb.

12. The powered prosthetic thumb of claim 1, wherein the mount is configured to couple with a partial prosthetic hand.

13. The powered prosthetic digit of claim 1, wherein the mount is configured to couple with an upper limb.

14. The powered prosthetic thumb of claim 13, wherein the upper limb is a prosthetic arm or natural arm.

15. A powered prosthetic thumb, comprising:
    a mount;
    a digit rotatably connected to the mount at least about a first axis;
    an actuator in mechanical communication with the digit and configured to rotate the digit about the first axis; and
    a clutch coupled with the mount and the digit, the clutch providing a rotational resistance to the digit about the first axis,
    wherein the digit is configured to be operated in a manual mode wherein the rotational resistance is overcome to allow the digit to be manually rotated about the first axis;
    wherein the clutch provides the rotational resistance to the digit about the first axis via a bevel gear.

16. The powered prosthetic thumb of claim 15, wherein the clutch comprises a compression spring.

17. The powered prosthetic thumb of claim 16, wherein the compression spring comprises a Belleville washer.

18. The powered prosthetic thumb of claim 15, wherein the digit is rotatably coupled with the mount about the first axis and a second axis, the first axis non-parallel with the second axis.

19. The powered prosthetic thumb of claim 18, wherein an orientation of the second axis relative to the mount changes as the digit rotates about the first axis.

20. The powered prosthetic thumb of claim 15, wherein the bevel gear is configured to rotate in response to overcoming the rotational resistance to allow the digit to be manually rotated about the first axis.

21. A powered prosthetic thumb comprising:
    a lower assembly comprising a mount;
    a middle assembly comprising a chassis, wherein the middle assembly is rotatably coupled with the lower assembly about a lateral axis;
    an upper assembly comprising a digit, wherein the upper assembly is rotatably coupled with the middle assembly about a pinch axis;
    a first actuator configured to cause rotation of the digit relative to the chassis about the pinch axis; and
    a second actuator configured to cause rotation of the digit about the lateral axis by causing rotation of the chassis relative to the mount about the lateral axis,
    wherein the first and second actuators are positioned at least partially within the digit, and
    wherein the pinch axis is configured to rotate about the lateral axis as the digit rotates about the lateral axis.

22. The powered prosthetic thumb of claim 21, wherein the lateral axis extends along a first direction, the pinch axis extends along a second direction that is non-parallel with respect to the first direction, and the second actuator is configured to cause rotation of the chassis relative to the mount about the lateral axis such that the second direction remains non-parallel to the first direction.

23. The powered prosthetic thumb of claim 21, wherein the lateral axis does not intersect the pinch axis while the chassis rotates about the lateral axis.

24. The powered prosthetic thumb of claim 21, wherein a proximal portion of the mount is positioned proximal to a distal portion of the chassis, a proximal portion of the chassis is positioned proximal to a distal portion of the digit, and the lateral axis is positioned proximal to the digit.

25. The powered prosthetic thumb of claim 24, wherein the lateral axis is positioned proximal to the chassis.

26. The powered prosthetic thumb of claim 24, wherein the pinch axis is positioned distal to the proximal portion of the chassis.

27. The powered prosthetic thumb of claim 24, wherein the digit is configured to rotate about the pinch axis in a first plane that comprises the lateral axis.

\* \* \* \* \*